(12) United States Patent
Basciano et al.

(10) Patent No.: US 11,351,163 B2
(45) Date of Patent: Jun. 7, 2022

(54) COMPOSITIONS AND METHODS OF TREATING CANCER

(71) Applicant: BRISTOL-MYERS SQUIBB COMPANY, Princeton, NJ (US)

(72) Inventors: Paul Andrew Basciano, Princeton, NJ (US); Justine Kamilah Walker, San Diego, CA (US); Penny E. Phillips, Princeton, NJ (US); Li Zhu, Princeton, NJ (US); Steven H. Bernstein, Lawrenceville, NJ (US); James Cassidy, Far Hills, NJ (US); Katy Lynn Simonsen, Princeton, NJ (US); Alexander Azrilevich, Princeton, NJ (US); Shivani Srivastava, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 141 days.

(21) Appl. No.: 16/649,277

(22) PCT Filed: Sep. 28, 2018

(86) PCT No.: PCT/US2018/053443
§ 371 (c)(1),
(2) Date: Mar. 20, 2020

(87) PCT Pub. No.: WO2019/067913
PCT Pub. Date: Apr. 4, 2019

(65) Prior Publication Data
US 2021/0030739 A1 Feb. 4, 2021

Related U.S. Application Data

(60) Provisional application No. 62/678,490, filed on May 31, 2018, provisional application No. 62/642,711, filed on Mar. 14, 2018, provisional application No. 62/609,210, filed on Dec. 21, 2017, provisional application No. 62/580,219, filed on Nov. 1, 2017, provisional application No. 62/569,766, filed on Oct. 9, 2017, provisional application No. 62/565,819, filed on Sep. 29, 2017.

(51) Int. Cl.
| | |
|---|---|
| *A61K 31/47* | (2006.01) |
| *A61P 35/00* | (2006.01) |
| *A61P 35/04* | (2006.01) |
| *A61K 9/00* | (2006.01) |
| *A61K 45/06* | (2006.01) |
| *C07K 16/28* | (2006.01) |

(52) U.S. Cl.
CPC ............ *A61K 31/47* (2013.01); *A61K 9/0019* (2013.01); *A61K 45/06* (2013.01); *A61P 35/04* (2018.01); *C07K 16/2818* (2013.01)

(58) Field of Classification Search
CPC .............................. A61K 31/47; A61P 35/00
USPC ......................................................... 514/311
See application file for complete search history.

(56) References Cited

U.S. PATENT DOCUMENTS

| | | | |
|---|---|---|---|
| 9,598,422 B2 | 3/2017 | Beck et al. | |
| 9,643,972 B2 | 5/2017 | Beck et al. | |
| 10,106,546 B2 | 10/2018 | Beck et al. | |
| 10,533,014 B2 | 1/2020 | Beck et al. | |
| 10,731,128 B2 * | 8/2020 | Borriello | .......... C07K 14/70578 |

FOREIGN PATENT DOCUMENTS

| | | |
|---|---|---|
| WO | 2016/073770 A1 | 5/2016 |
| WO | 2017/079669 A1 | 5/2017 |

OTHER PUBLICATIONS

US Department of Health and Human Services, Food and Drug Administration. "Clinical Trial Endpoints for the Approval of Cancer Drugs and Biologies", May 2007, entire document.
Dashyant Dhanak et al.: "Small-Molecule Targets in ImmunoOncology", Cell Chemical Biology, vol. 24, No. 9, Sep. 21, 2017 (Sep. 21, 2017), pp. 1148-1160.
George C. Prendergast et al.: "Indoleamine 2,3-Dioxygenase and Its Therapeutic Inhibition in Cancer In: International review of cell and molecular biology", Sep. 21, 2017 (Sep. 21, 2017), Elsevier, Amsterdam, XP055698724, ISSN: 1937-6448 vol. 336, pp. 175-203.
M. Moscoso Castro et al.: "American Association for Cancer Research (AACR)—108th Annual Meeting. Washington, D.C., USA—Apr. 1-5, 2017", Drugs of the Future, vol. 42, No. 6, Apr. 5, 2017 (Apr. 5, 2017), pp. 359-366.
Siu Lillian et al.: "Abstract CT116: BMS-986205, an optimized indoleamine 2,3-dioxygenase 1 (IDO1) inhibitor, is well tolerated with potent pharmacodynamic (PD) activity, alone and in combination with nivolumab (nivo) in advanced cancers in a phase 1/2a trial | Cancer Research", Cancer Trials, Jul. 1, 2017 (Jul. 1, 2017), XP55801477, Retrieved from the Internet: URL:https://cancerres.aacrjournals.org/content/77/13_Supplement/CT116 [retrieved on May 4, 2021].

* cited by examiner

*Primary Examiner* — Raymond J Henley, III
(74) *Attorney, Agent, or Firm* — BakerHostetler

(57) ABSTRACT

The disclosure is directed to methods of treating cancer in subjects with a combination of a monoclonal antibody and (R)-N-(4-chlorophenyl)-2-(cis-4-(6-fluoroquinolin-4-yl)cyclohexyl)propanamide, or a salt thereof.

19 Claims, 5 Drawing Sheets

COMPOSITIONS AND METHODS OF TREATING CANCER

CROSS-REFERENCE TO RELATED APPLICATIONS

This application is the National Stage Application of International Patent Application No. PCT/US2018/053443 filed Sep. 28, 2018, which claims the benefit of U.S. Provisional Patent Application No. 62/565,819, filed Sep. 29, 2017, U.S. Provisional Patent Application No. 62/569,766, filed Oct. 9, 2017, U.S. Provisional Patent Application No. 62/580,219, filed Nov. 1, 2017, U.S. Provisional Patent Application No. 62/609,210, filed Dec. 21, 2017, U.S. Provisional Patent Application No. 62/642,711, filed Mar. 14, 2018, and U.S. Provisional Patent Application No. 62/678,490, filed May 31, 2018, the entireties of which are incorporated herein by reference.

TECHNICAL FIELD

The disclosure is directed to methods of treating cancer in subjects with a combination of a monoclonal antibody and (R)-N-(4-chlorophenyl)-2-(cis-4-(6-fluoroquinolin-4-yl)cyclohexyl)propanamide, or a salt thereof.

BACKGROUND

Checkpoint inhibitors have transformed cancer care, but extending those benefits to more patients may require additional approaches. Indoleamine 2,3-dioxygenase (IDO; also known as IDO1) allows tumor escape through kynurenine production, which decreases immune cell tumor infiltration/function and increases regulatory T cell numbers. In addition to cancer, IDO has been implicated in, among other conditions, immunosuppression, chronic infections, and autoimmune diseases or disorders (e.g. rheumatoid arthritis). Thus, suppression of tryptophan degradation by inhibition of IDO activity has tremendous therapeutic value. Moreover, inhibitors of IDO can be used to enhance T cell activation when the T cells are suppressed by pregnancy, malignancy, or a virus (e.g., HIV).

New cancer treatment methods are needed.

SUMMARY

The disclosure is directed to, among other things, methods of treating cancer in a subject comprising administering to the subject a combination of a monoclonal antibody and a compound of Formula I, or a pharmaceutically acceptable salt thereof, or a combination thereof,

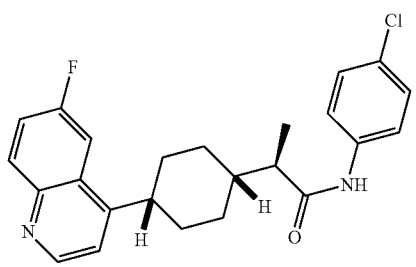

(I)

(R)-N-(4-chlorophenyl)-2-(cis-4-(6-fluoroquinolin-4-yl)cyclohexyl)propanamide wherein the amount of the compound administered to the subject is from about 100 mg per day to about 200 mg per day.

DETAILED DESCRIPTION OF ILLUSTRATIVE EMBODIMENTS

Figure 1A:
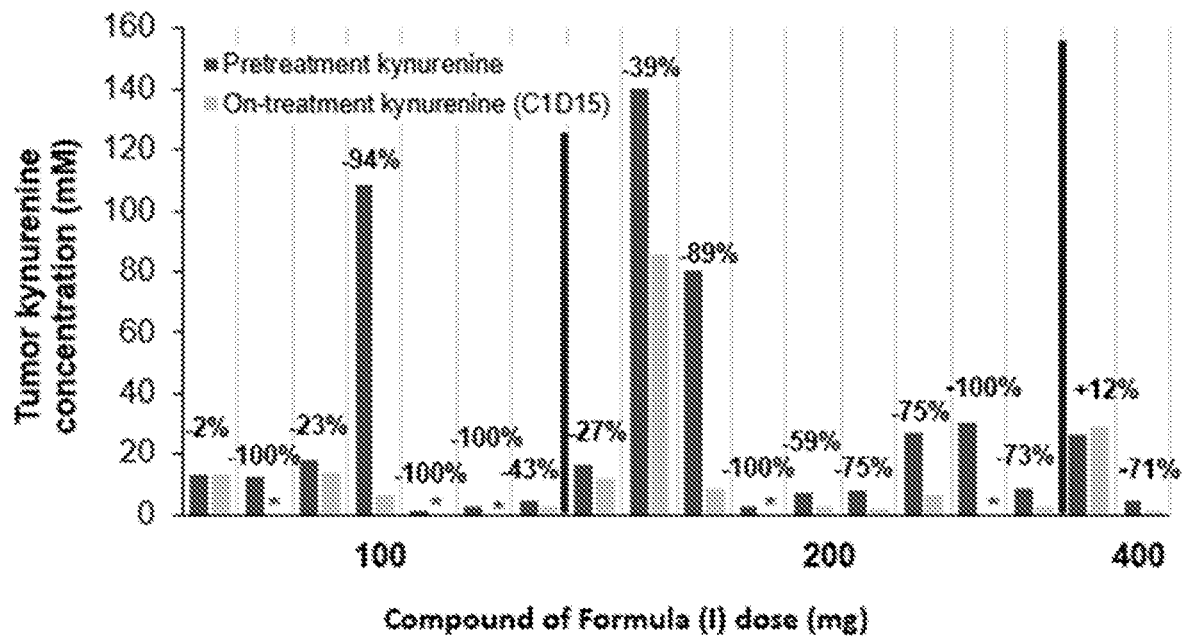
FIG. 1A illustrates intratumoral kynurenine concentrations at 100 mg, 200 mg or 400 mg of the compound of Formula (I).

The present disclosure may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise.

As used in the specification and in the claims, the term "comprising" may include the embodiments "consisting of" and "consisting essentially of." The terms "comprise(s)," "include(s)," "having," "has," "can," "contain(s)," and variants thereof, as used herein, are intended to be open-ended transitional phrases, terms, or words that require the presence of the named ingredients/steps and permit the presence of other ingredients/steps. However, such description should be construed as also describing compositions or processes as "consisting of" and "consisting essentially of" the enumerated compounds, which allows the presence of only the named compounds, along with any pharmaceutically carriers, and excludes other compounds.

All ranges disclosed herein are inclusive of the recited endpoint and independently combinable (for example, the range of "from 100 mg to 200 mg" is inclusive of the endpoints, 100 mg and 200 mg, and all the intermediate values). The endpoints of the ranges and any values disclosed herein are not limited to the precise range or value; they are sufficiently imprecise to include values approximating these ranges and/or values.

As used herein, approximating language may be applied to modify any quantitative representation that may vary without resulting in a change in the basic function to which it is related. Accordingly, a value modified by a term or terms, such as "about" and "substantially," may not be limited to the precise value specified, in some cases. In at least some instances, the approximating language may correspond to the precision of an instrument for measuring the value. The modifier "about" should also be considered as disclosing the range defined by the absolute values of the two endpoints. For example, the expression "from about 100 to about 200" also discloses the range "from 100 to 200." The term "about" may refer to plus or minus 10% of the indicated number. For example, "about 10%" may indicate a range of 9% to 11%, and "about 1" may mean from 0.9 to 1.1. Other meanings of "about" may be apparent from the context, such as rounding off, so, for example "about 1" may also mean from 0.5 to 1.4.

The disclosure is directed to methods of treating cancer in a subject comprising administering to the subject a combination of a monoclonal antibody and a compound of Formula I, or a pharmaceutically acceptable salt thereof, or a combination thereof,

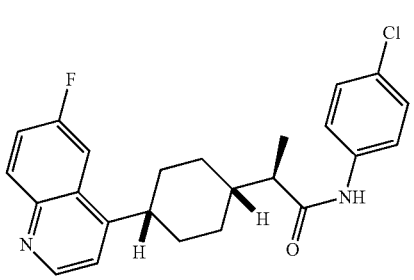

(R)-N-(4-chlorophenyl)-2-(cis-4-(6-fluoroquinolin-4-yl)cyclohexyl)propanamide wherein the amount of the compound administered to the subject may be from about 100 mg per day to about 200 mg per day. For example, the amount of the compound of Formula I, or pharmaceutically acceptable salt thereof, administered to the subject may be about 100, 110, 120, 130, 140, 150, 160, 170, 180, 190 or 200 mg per day.

In certain embodiments, the amount of the compound of Formula I, or pharmaceutically acceptable salt thereof, or a combination thereof, administered to the subject may be from about 25 mg per day to about 400 mg per day, about 50 mg per day to about 400 mg per day, about 75 mg per day to about 400 mg per day, about 100 mg per day to about 400 mg per day, about 200 mg per day to about 400 mg per day, 25 mg per day to about 200 mg per day, about 50 mg per day to about 200 mg per day, about 75 mg per day to about 200 mg per day, about 100 mg per day to about 200 mg per day, about 25 mg per day to about 100 mg per day, about 50 mg per day to about 100 mg per day, about 75 mg per day to about 100 mg per day, about 25 mg per day to about 75 mg per day, about 50 mg per day to about 75 mg per day, or about 25 mg per day to about 50 mg per day.

In certain embodiments, the amount of the compound of Formula I, or pharmaceutically acceptable salt thereof, or a combination thereof, administered to the subject may be about 25 mg per day. In certain embodiments, the amount of the compound of Formula I, or pharmaceutically acceptable salt thereof, or a combination thereof, administered to the subject may be about 50 mg per day. In certain embodiments, the amount of the compound of Formula I, or pharmaceutically acceptable salt thereof, or a combination thereof, administered to the subject may be about 75 mg per day. In certain embodiments, the amount of the compound of Formula I, or pharmaceutically acceptable salt thereof, or a combination thereof, administered to the subject may be about 100 mg per day. In certain embodiments, the amount of the compound of Formula I, or pharmaceutically acceptable salt thereof, or a combination thereof, administered to the subject may be about 125 mg per day. In certain embodiments, the amount of the compound of Formula I, or pharmaceutically acceptable salt thereof, or a combination thereof, administered to the subject may be about 150 mg per day. In certain embodiments, the amount of the compound of Formula I, or pharmaceutically acceptable salt thereof, or a combination thereof, administered to the subject may be about 200 mg per day. In certain embodiments, the amount of the compound of Formula I, or pharmaceutically acceptable salt thereof, or a combination thereof, administered to the subject may be about 400 mg per day.

The amounts of the compound of Formula I described herein are based on the free form of the compound of Formula I, that is, the non-salt form. If salts are administered, the amounts need to be calculated as a function of the molecular weight ratio between the salt and the free form.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia, for use in animals, and more particularly, in humans.

"Pharmaceutically acceptable salt" refers to a salt of a compound of the disclosure that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non-toxic organic or inorganic acids, such as hydrochloride, hydrobromide, tartrate, mesylate, acetate, maleate, oxalate and the like. In some embodiments, the salt of Formula I is a hydrochloric acid salt. In some embodiments, the salt of Formula I is a hydrobromic acid salt. In some embodiments, the salt of Formula I is a fumaric acid salt. In some embodiments, the salt of Formula I is a succinic acid salt. In preferred embodiments, the salt of Formula I is a methanesulfonic acid (MSA) salt.

In some embodiments, the compound of the disclosure is in the form of a free base. In some embodiments, the compound of the disclosure is a mixture of a free base and a pharmaceutically acceptable salt. For example, the compound of the disclosure may be about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% free base. Alternatively, the compound of the disclosure may be about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in the form of a pharmaceutically acceptable salt.

"Pharmaceutically acceptable excipient" refers to a diluent, adjuvant, excipient or carrier with which a compound of the disclosure is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, stearates, silicon dioxide, polyvinyl alcohols, talc, titanium dioxide, ferric oxide, and polyethylene glycols.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

The term "antibody," and like terms is meant in a broad sense and includes immunoglobulin molecules including, monoclonal antibodies (such as murine, human, human-adapted, humanized, and chimeric monoclonal antibodies), antibody fragments, bispecific or multispecific antibodies, dimeric, tetrameric or multimeric antibodies, and single chain antibodies. Immunoglobulins can be assigned to five major classes, namely IgA, IgD, IgE, IgG, and IgM, depending on the heavy chain constant domain amino acid sequence. IgA and IgG are further sub-classified as the isotypes IgA1, IgA2, IgG1, IgG2, IgG3, and IgG4. Antibody light chains of any vertebrate species can be assigned to one of two clearly distinct types, namely kappa (κ) and lambda (λ), based on the amino acid sequences of their constant domains.

"Monoclonal antibody" refers to a population of antibody molecules of a single molecular composition. A monoclonal antibody composition displays a single binding specificity and affinity for a particular epitope, or in a case of a bispecific monoclonal antibody, a dual binding specificity to two distinct epitopes. Monoclonal antibody therefore refers to an antibody population with single amino acid composition in each heavy and each light chain, except for possible well known alterations such as removal of C-terminal lysine from the antibody heavy chain. Monoclonal antibodies may have heterogeneous glycosylation within the antibody population. Monoclonal antibody may be monospecific or multispecific, or monovalent, bivalent or multivalent. A bispecific antibody is included in the term monoclonal antibody.

Anti-PD-1 Antibodies Useful for the Invention

Any anti-PD-1 antibody that is known in the art can be used in the presently described methods. In particular, various human monoclonal antibodies that bind specifically to PD-1 with high affinity have been disclosed in U.S. Pat. No. 8,008,449. Each of the anti-PD-1 humanized antibodies disclosed in U.S. Pat. No. 8,008,449 has been demonstrated to exhibit one or more of the following characteristics: (a) binds to human PD-1 with a $K_D$ of $1\times10^{-7}$ M or less, as determined by surface plasmon resonance using a Biacore biosensor system; (b) does not substantially bind to human CD28, CTLA-4 or ICOS; (c) increases T-cell proliferation in a Mixed Lymphocyte Reaction (MLR) assay; (d) increases interferon-γ production in an MLR assay; (e) increases IL-2 secretion in an MLR assay; (f) binds to human PD-1 and cynomolgus monkey PD-1; (g) inhibits the binding of PD-L1 and/or PD-L2 to PD-1; (h) stimulates antigen-specific memory responses; (i) stimulates antibody responses; and (j) inhibits tumor cell growth in vivo. Anti-PD-1 antibodies usable in the present invention include monoclonal antibodies that bind specifically to human PD-1 and exhibit at least one, in some embodiments, at least five, of the preceding characteristics.

Other anti-PD-1 monoclonal antibodies have been described in, for example, U.S. Pat. Nos. 6,808,710, 7,488, 802, 8,168,757 and 8,354,509, US Publication No. 2016/0272708, and PCT Publication Nos. WO 2012/145493, WO 2008/156712, WO 2015/112900, WO 2012/145493, WO 2015/112800, WO 2014/206107, WO 2015/35606, WO 2015/085847, WO 2014/179664, WO 2017/020291, WO 2017/020858, WO 2016/197367, WO 2017/024515, WO 2017/025051, WO 2017/123557, WO 2016/106159, WO 2014/194302, WO 2017/040790, WO 2017/133540, WO 2017/132827, WO 2017/024465, WO 2017/025016, WO 2017/106061, each of which is incorporated by reference in its entirety.

In some embodiments, the anti-PD-1 antibody is selected from the group consisting of nivolumab (also known as "OPDIVO"; formerly designated 5C4, BMS-936558, MDX-1106, or ONO-4538), pembrolizumab (Merck, also known as "KEYTRUDA", lambrolizumab, and MK-3475. See WO2008156712A1), PDR001 (Novartis; see WO 2015/112900), MEDI-0680 (Astrazenica; AMP-514; see WO 2012/145493), REGN-2810 (Regeneron; see WO 2015/112800), JS001 (TAIZHOU JUNSHI PHARMA; see Si-Yang Liu et al., *J. Hematol. Oncol.* 10:136 (2017)), BGB-A317 (Beigene; see WO 2015/35606 and US 2015/0079109), INCSHR1210 (SHR-1210; Jiangsu Hengrui Medicine; see WO 2015/085847; Si-Yang Liu et al., *J. Hematol. Oncol.* 10:136 (2017)), TSR-042 (ANB011; Tesaro Biopharmaceutical; see WO2014/179664), GLS-010 (WBP3055; Wuxi/Harbin Gloria Pharmaceuticals; see Si-Yang Liu et al., *J. Hematol. Oncol.* 10:136 (2017)), AM-0001 (Armo), STI-1110 (Sorrento Therapeutics; see WO 2014/194302), AGEN2034 (Agenus; see WO 2017/040790), and MGD013 (Macrogenics).

In one embodiment, the anti-PD-1 antibody is nivolumab. Nivolumab is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9):846-56).

In another embodiment, the anti-PD-1 antibody is pembrolizumab. Pembrolizumab is a humanized monoclonal IgG4 antibody directed against human cell surface receptor PD-1 (programmed death-1 or programmed cell death-1). Pembrolizumab is described, for example, in U.S. Pat. Nos. 8,354,509 and 8,900,587; see also www.cancer.gov/drugdictionary?cdrid=695789 (last accessed: Dec. 14, 2014). Pembrolizumab has been approved by the FDA for the treatment of relapsed or refractory melanoma.

Anti-PD-1 antibodies usable in the disclosed methods also include isolated antibodies that bind specifically to human PD-1 and cross-compete for binding to human PD-1 with any anti-PD-1 antibody disclosed herein, e.g., nivolumab (see, e.g., U.S. Pat. Nos. 8,008,449 and 8,779,105; WO 2013/173223). In some embodiments, the anti-PD-1 antibody binds the same epitope as any of the anti-PD-1 antibodies described herein, e.g., nivolumab. The ability of antibodies to cross-compete for binding to an antigen indicates that these monoclonal antibodies bind to the same epitope region of the antigen and sterically hinder the binding of other cross-competing antibodies to that particular epitope region. These cross-competing antibodies are expected to have functional properties very similar those of the reference antibody, e.g., nivolumab, by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 antibody, nivolumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-1 antibodies usable in the methods of the disclosed invention also include antigen-binding portions of the above antibodies. It has been amply demonstrated that the antigen-binding function of an antibody can be performed by fragments of a full-length antibody.

Anti-PD-1 antibodies suitable for use in the disclosed methods or compositions are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and up-regulating the immune system. In certain embodiments, the anti-PD-1 antibody or antigen-binding portion thereof cross-competes with nivolumab for binding to human PD-1.

Anti-PD-L1 Antibodies Useful for the Invention

Any anti-PD-L1 antibody can be used in the methods of the present disclosure. Examples of anti-PD-L1 antibodies useful in the methods of the present disclosure include the antibodies disclosed in U.S. Pat. No. 9,850,507. Each of the anti-PD-L1 human monoclonal antibodies disclosed in U.S. Pat. No. 9,850,507 have been demonstrated to exhibit one or more of the following characteristics: (a) binds to human PD-L1 with a $K_D$ of $1 \times 10^{-7}$ M or less, as determined by surface plasmon resonance using a Biacore biosensor system; (b) increases T-cell proliferation in a Mixed Lymphocyte Reaction (MLR) assay; (c) increases interferon-γ production in an MLR assay; (d) increases IL-2 secretion in an MLR assay; (e) stimulates antibody responses; and (f) reverses the effect of T regulatory cells on T cell effector cells and/or dendritic cells. Anti-PD-L1 antibodies usable in the present invention include monoclonal antibodies that bind specifically to human PD-L1 and exhibit at least one, in some embodiments, at least five, of the preceding characteristics.

In certain embodiments, the anti-PD-L1 antibody is selected from the group consisting of BMS-936559 (formerly 12A4 or MDX-1105; see, e.g., U.S. Pat. No. 7,943,743 and WO 2013/173223), MPDL3280A (also known as RG7446, atezolizumab, and TECENTRIQ; U.S. Pat. No. 8,217,149; see, also, Herbst et al. (2013) J Clin Oncol 31(suppl):3000), durvalumab (IMFINZI; MEDI-4736; Astrazenica; see WO 2011/066389), avelumab (Pfizer; MSB-0010718C; BAVENCIO; see WO 2013/079174), STI-1014 (Sorrento; see WO2013/181634), CX-072 (Cytomx; see WO2016/149201), KN035 (3D Med/Alphamab; see Zhang et al., *Cell Discov.* 7:3 (March 2017), LY3300054 (Eli Lilly Co.; see, e.g, WO 2017/034916), and CK-301 (Checkpoint Therapeutics; see Gorelik et al., AACR:Abstract 4606 (April 2016)).

In certain embodiments, the PD-L1 antibody is atezolizumab (TECENTRIQ). Atexolizumab is a fully humanized IgG1 monoclonal anti-PD-L1 antibody.

In certain embodiments, the PD-L1 antibody is durvalumab (IMFINZI). Durvalumab is a human IgG1 kappa monoclonal anti-PD-L1 antibody.

In certain embodiments, the PD-L1 antibody is avelumab (BAVENCIO). Avelumab is a human IgG1 lambda monoclonal anti-PD-L1 antibody.

In other embodiments, the anti-PD-L1 monoclonal antibody is selected from the group consisting of 28-8, 28-1, 28-12, 29-8, 5H1, and any combination thereof.

Anti-PD-L1 antibodies usable in the disclosed methods also include isolated antibodies that bind specifically to human PD-L1 and cross-compete for binding to human PD-L1 with any anti-PD-L1 antibody disclosed herein, e.g., atezolizumab and/or avelumab. In some embodiments, the anti-PD-L1 antibody binds the same epitope as any of the anti-PD-L1 antibodies described herein, e.g., atezolizumab and/or avelumab. The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of the reference antibody, e.g., atezolizumab and/or avelumab, by virtue of their binding to the same epitope region of PD-L1. Cross-competing antibodies can be readily identified based on their ability to cross-compete with atezolizumab and/or avelumab in standard PD-L1 binding assays such as Biacore analysis, ELISA assays or flow cytometry (see, e.g., WO 2013/173223).

In certain embodiments, the antibodies that cross-compete for binding to human PD-L1 with, or bind to the same epitope region of human PD-L1 antibody as, atezolizumab and/or avelumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-L1 antibodies usable in the methods of the disclosed invention also include antigen-binding portions of the above antibodies. It has been amply demonstrated that the antigen-binding function of an antibody can be performed by fragments of a full-length antibody.

Anti-PD-L1 antibodies suitable for use in the disclosed methods or compositions are antibodies that bind to PD-L1 with high specificity and affinity, block the binding of PD-1, and inhibit the immunosuppressive effect of the PD-1 signaling pathway. In any of the compositions or methods disclosed herein, an anti-PD-L1 "antibody" includes an antigen-binding portion or fragment that binds to PD-L1 and exhibits the functional properties similar to those of whole antibodies in inhibiting receptor binding and up-regulating the immune system. In certain embodiments, the anti-PD-L1 antibody or antigen-binding portion thereof cross-competes with atezolizumab and/or avelumab for binding to human PD-L1.

Anti-CTLA-4 Antibodies Useful for the Invention

Any anti-CTLA-4 antibody that is known in the art can be used in the methods of the present disclosure. Anti-CTLA-4 antibodies of the instant invention bind to human CTLA-4 so as to disrupt the interaction of CTLA-4 with a human B7 receptor. Because the interaction of CTLA-4 with B7 transduces a signal leading to inactivation of T-cells bearing the CTLA-4 receptor, disruption of the interaction effectively induces, enhances or prolongs the activation of such T cells, thereby inducing, enhancing or prolonging an immune response.

Human monoclonal antibodies that bind specifically to CTLA-4 with high affinity have been disclosed in U.S. Pat. Nos. 6,984,720 and 7,605,238. Other anti-CTLA-4 monoclonal antibodies have been described in, for example, U.S. Pat. Nos. 5,977,318, 6,051,227, 6,682,736, and 7,034,121 and International Publication Nos. WO 2012/122444, WO 2007/113648, WO 2016/196237, and WO 2000/037504, each of which is incorporated by reference herein in its entirety. The anti-CTLA-4 human monoclonal antibodies disclosed in U.S. Pat. Nos. 6,984,720 and 7,605,238 have been demonstrated to exhibit one or more of the following characteristics: (a) binds specifically to human CTLA-4 with a binding affinity reflected by an equilibrium association constant ($K_a$) of at least about $10^7$ $M^{-1}$, or about $10^9$ $M^{-1}$, or about $10^{10}$ $M^{-1}$ to $10^{11}$ $M^{-1}$ or higher, as determined by Biacore analysis; (b) a kinetic association constant ($k_a$) of at least about $10^3$, about $10^4$, or about $10^5$ $m^{-1}$ $s^{-1}$; (c) a kinetic disassociation constant ($k_d$) of at least about $10^3$, about $10^4$, or about $10^5$ $m^{-1}$ $s^{-1}$; and (d) inhibits the binding of CTLA-4 to B7-1 (CD80) and B7-2 (CD86). Anti-CTLA-4 antibodies useful for the present invention include monoclonal antibodies that bind specifically to human CTLA-4 and exhibit at least one, at least two, or at least three of the preceding characteristics.

In certain embodiments, the CTLA-4 antibody is selected from the group consisting of ipilimumab (YERVOY; U.S. Pat. No. 6,984,720), MK-1308 (Merck), AGEN-1884 (Agenus Inc.; WO 2016/196237), and tremelimumab (formerly ticilimumab, CP-675,206; Astrazenica; see, e.g., WO 2000/037504 and Ribas, *Update Cancer Ther.* 2(3): 133-39 (2007)). In particular embodiments, the anti-CTLA-4 antibody is ipilimumab.

In particular embodiments, the CTLA-4 antibody is the human monoclonal antibody 10D1 (now known as ipilimumab and marketed as YERVOY) as disclosed in U.S. Pat. No. 6,984,720. Ipilimumab is an anti-CTLA-4 antibody for use in the methods disclosed herein. Ipilimumab is a fully human, IgG1 monoclonal antibody that blocks the binding of CTLA-4 to its B7 ligands, thereby stimulating T cell activation and improving overall survival (OS) in patients with advanced melanoma.

In particular embodiments, the CTLA-4 antibody is tremelimumab (also known as CP-675,206). Tremelimumab is human IgG2 monoclonal anti-CTLA-4 antibody. Tremelimumab is described in WO/2012/122444, U.S. Publ. No. 2012/263677, or WO Publ. No. 2007/113648 A2.

In particular embodiments, the CTLA-4 antibody is MK-1308, which is an anti-CTLA-4 antibody under development by Merck.

In particular embodiments, the CTLA-4 antibody is AGEN-1884, which is a recombinant human monoclonal antibody to human CTLA-4, developed by Agenus Inc.

Anti-CTLA-4 antibodies usable in the disclosed methods also include isolated antibodies that bind specifically to human CTLA-4 and cross-compete for binding to human CTLA-4 with any anti-CTLA-4 antibody disclosed herein, e.g., ipilimumab and/or tremelimumab. In some embodiments, the anti-CTLA-4 antibody binds the same epitope as any of the anti-CTLA-4 antibodies described herein, e.g., ipilimumab and/or tremelimumab. The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of the reference antibody, e.g., ipilimumab and/or tremelimumab, by virtue of their binding to the same epitope region of CTLA-4. Cross-competing antibodies can be readily identified based on their ability to cross-compete with ipilimumab and/or tremelimumab in standard CTLA-4 binding assays such as Biacore analysis, ELISA assays or flow cytometry (see, e.g., WO 2013/173223).

In certain embodiments, the antibodies that cross-compete for binding to human CTLA-4 with, or bind to the same epitope region of human CTLA-4 antibody as, ipilimumab and/or tremelimumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-CTLA-4 antibodies usable in the methods of the disclosed invention also include antigen-binding portions of the above antibodies. It has been amply demonstrated that the antigen-binding function of an antibody can be performed by fragments of a full-length antibody.

Anti-CTLA-4 antibodies suitable for use in the disclosed methods or compositions are antibodies that bind to CTLA-4 with high specificity and affinity, block the activity of CTLA-4, and disrupt the interaction of CTLA-4 with a human B7 receptor. In any of the compositions or methods disclosed herein, an anti-CTLA-4 "antibody" includes an antigen-binding portion or fragment that binds to CTLA-4 and exhibits the functional properties similar to those of whole antibodies in inhibiting the interaction of CTLA-4 with a human B7 receptor and up-regulating the immune system. In certain embodiments, the anti-CTLA-4 antibody or antigen-binding portion thereof cross-competes with ipilimumab and/or tremelimumab for binding to human CTLA-4.

Anti-Lag-3 Antibodies Useful for the Invention

Any anti-LAG-3 antibody can be used in the methods of the present disclosure. Examples of LAG-3 antibodies useful in the methods of the present disclosure include, for example, relatlimab (BMS-986016 or MDX-1408) described in WO2010/019570 and WO2014/008218 or IMP-731 or IMP-321, described in US2011/007023, WO08/132601 and WO09/44273. Anti-LAG-3 antibodies that compete with and/or bind to the same epitope as that of any of these antibodies may able be used in combination treatments.

In certain embodiments, the anti-LAG-3 antibody is relatlimab (BMS-986016 or MDX-1408).

In certain embodiments, the anti-LAG-3 antibody binds to human LAG-3 with a $K_D$ of $5\times10^{-8}$ M or less, binds to human LAG-3 with a $K_D$ of $1\times10^{-8}$ M or less, binds to human LAG-3 with a $K_D$ of $5\times10^{-9}$ M or less, or binds to human LAG-3 with a $K_D$ of between $1\times10^{-8}$ M and $1\times10^{-10}$ M or less.

Anti-LAG-3 antibodies usable in the disclosed methods also include isolated antibodies that bind specifically to human LAG-3 and cross-compete for binding to human LAG-3 with any anti-LAG-3 antibody disclosed herein, e.g., relatlimab. In some embodiments, the anti-LAG-3 antibody binds the same epitope as any of the anti-LAG-3 antibodies described herein, e.g., relatlimab. The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of the reference antibody, e.g., relatlimab, by virtue of their binding to the same epitope region of LAG-3. Cross-competing antibodies can be readily identified based on their ability to cross-compete with relatlimab in standard LAG-3 binding assays such as Biacore analysis, ELISA assays or flow cytometry.

In certain embodiments, the antibodies that cross-compete for binding to human LAG-3 with, or bind to the same epitope region of human LAG-3 antibody as, relatlimab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti- LAG-3 antibodies usable in the methods of the disclosed invention also include antigen-binding portions of the above antibodies. It has been amply demonstrated that the antigen-binding function of an antibody can be performed by fragments of a full-length antibody.

Anti- LAG-3 antibodies suitable for use in the disclosed methods or compositions are antibodies that bind to LAG-3 with high specificity and affinity. In any of the compositions or methods disclosed herein, an anti-LAG-3 "antibody" includes an antigen-binding portion or fragment that binds to LAG-3 and exhibits the functional properties similar to those of whole antibodies. In certain embodiments, the anti-LAG-3 antibody or antigen-binding portion thereof cross-competes with relatlimab for binding to human LAG-3.

Combination Therapies

As used herein, "combination" is meant to include therapies that can be administered separately, for example, formulated separately for separate administration (e.g., as may be provided in a kit), and therapies that can be administered together in a single formulation (i.e., a "co-formulation"). In certain aspects, the monoclonal antibody and the compound of Formula I, or pharmaceutically acceptable salt thereof, are administered or applied sequentially, e.g., where one agent is administered prior to one or more other agents. In other embodiments, the monoclonal antibody and the compound of Formula I, or pharmaceutically acceptable salt thereof, are administered simultaneously, e.g. , where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present disclosure.

In some aspects, the antibody is ipilimumab. Ipilimumab may be administered by intravenous infusion at a dose of about 1 mg/kg to 10 mg/kg every 3 weeks. For example, the ipilimumab may be administered to the subject by intravenous infusion at a dose of about 1 mg/kg, 2 mg/kg, 3 mg/kg, 4 mg/kg, 5 mg/kg, 6 mg/kg, 7 mg/kg, 8 mg/kg, 9 mg/kg or 10 mg/kg every 3 weeks. In preferred aspects, the ipilimumab may be administered by intravenous infusion at a dose of about 3 mg/kg every 3 weeks.

In other aspects, the ipilimumab may be administered by intravenous infusion at a dose of about 1 mg/kg every 5 to 10 weeks. For example, the ipilimumab may be administered to the subject by intravenous infusion at a dose of about 1 mg/kg ever 5, 6, 7, 8, 9 or 10 weeks. In preferred aspects, the ipilimumab may be administered by intravenous infusion at a dose of about 1 mg/kg every 6 weeks. In other preferred aspects, the ipilimumab may be administered by intravenous infusion at a dose of about 1 mg/kg every 8 weeks.

In some aspects of the disclosure, the antibody is nivolumab. Nivolumab may be administered to the subject by intravenous infusion at a dose of about 80 mg to 360 mg every 3 weeks. For example, the nivolumab may be administered to the subject by intravenous infusion at a dose of about 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, or about 360 mg every 3 weeks. In preferred aspects, nivolumab may be administered by intravenous infusion at a dose of about 80 mg every 3 weeks. In other preferred aspects, the nivolumab is administered by intravenous infusion at a dose of about 360 mg every 3 weeks The nivolumab concentrations disclosed in this paragraph are hereby disclosed in combination with ipilimumab concentrations disclosed herein. Thus, the nivolumab concentrations disclosed in this paragraph are hereby disclosed in combination with ipilimumab concentrations of about 1 mg/kg to about 10 mg/kg. For the sake of brevity, all of the combinations are not being parsed out.

In other aspects, the nivolumab may be administered by intravenous infusion at a dose of about 200 mg to 300 mg every 2 weeks. For example, the nivolumab may be administered to the subject by intravenous infusion at a dose of about 200 mg, 210 mg, 220 mg, 230 mg, 240 mg, 250 mg, 260 mg, 270 mg, 280 mg, 290 mg, or about 300 mg every 2 weeks. In preferred aspects, the nivolumab may be administered by intravenous infusion at a dose of about 240 mg every 2 weeks. The nivolumab concentrations disclosed in this paragraph are hereby disclosed in combination with ipilimumab concentrations disclosed herein. Thus, the nivolumab concentrations disclosed in this paragraph are hereby disclosed in combination with ipilimumab concentrations of about 1 mg/kg to about 10 mg/kg. For the sake of brevity, all of the combinations are not being parsed out.

In further aspects, the nivolumab may be administered by intravenous infusion at a dose of about 400 mg to 500 mg every 4 weeks. For example, the nivolumab may be administered to the subject by intravenous infusion at a dose of about 400 mg, 410 mg, 420 mg, 430 mg, 440 mg, 450 mg, 460 mg, 470 mg, 480 mg, 490 mg, or about 500 mg every 4 weeks. In preferred aspects, the nivolumab may be administered by intravenous infusion at a dose of about 480 mg every 4 weeks. The nivolumab concentrations disclosed in this paragraph are hereby disclosed in combination with ipilimumab concentrations disclosed herein. Thus, the nivolumab concentrations disclosed in this paragraph are hereby disclosed in combination with ipilimumab concentrations of about 1 mg/kg to about 10 mg/kg. For the sake of brevity, all of the combinations are not being parsed out.

In some aspects, the nivolumab is further administered with ipilimumab, wherein the ipilimumab may be administered by intravenous infusion at a dose of about 1 mg/kg to 10 mg/kg every 3 weeks. For example, the ipilimumab may be administered to the subject by intravenous infusion at a dose of about 1 mg/kg, 2 mg/kg, 3 mg/kg, 4 mg/kg, 5 mg/kg, 6 mg/kg, 7 mg/kg, 8 mg/kg, 9 mg/kg or 10 mg/kg every 3 weeks. In preferred aspects, the ipilimumab may be administered by intravenous infusion at a dose of about 3 mg/kg every 3 weeks.

In some aspects of the disclosure, the antibody is relatlimab. Relatlimab may be administered to the subject by intravenous infusion at a therapeutically effective dose. The relatlimab concentrations disclosed herein are hereby disclosed in combination with the ipilimumab and the nivolumab concentrations disclosed herein.

In further aspects, the ipilimumab may be administered by intravenous infusion at a dose of about 1 mg/kg every 5 to 10 weeks. For example, the ipilimumab may be administered to the subject by intravenous infusion at a dose of about 1 mg/kg ever 5, 6, 7, 8, 9 or 10 weeks. In preferred aspects, the ipilimumab may be administered by intravenous infusion at a dose of about 1 mg/kg every 6 weeks. In other preferred aspects, the ipilimumab may be administered by intravenous infusion at a dose of about 1 mg/kg every 8 weeks.

For example, the compound of Formula I, administered orally at a dose of 100 or 200 mg once daily, may be administered in combination with nivolumab, administered by intravenous infusion at a dose of about 240 mg every 2 weeks or 480 mg every 4 weeks, optionally administered in further combination with ipilimumab, administered at a dose of 1 mg/kg every 8 weeks. This treatment regimen, for example, may be used for treating cancer in a subject wherein the cancer is a cervical cancer, diffuse large B-cell lymphoma, non-small cell lung cancer, renal cell carcinoma, squamous cell carcinoma of the head and neck, bladder cancer, pancreatic cancer, melanoma, ASST, sarcoma, or endometrial and breast cancer. In preferred embodiments, the cancer is melanoma.

By way of further example, the compound of Formula I, administered orally at a dose of 100 or 200 mg once daily, may be administered in combination with nivolumab, administered by intravenous infusion at a dose of about 360 mg every 3 weeks, optionally administered in further combination with ipilimumab, administered at a dose of 1 mg/kg every 6 weeks. This treatment regimen, for example, may be used for treating cancer in a subject wherein the cancer is non-small cell lung cancer (NSCLC). In some embodiments, the NSCLC is stage IV or recurrent NSCLC. In some embodiments, the NSCLC is previously untreated stage IV or recurrent NSCLC.

By way of still further example, the compound of Formula I, administered orally at a dose of 100 or 200 mg once daily, may be administered in combination with nivolumab, administered by intravenous infusion at a dose of about 80 mg every 3 weeks, in further combination with ipilimumab, administered at a dose of 3 mg/kg every 3 weeks for a total of four treatments, followed by administration by intravenous infusion of nivolumab at 480 mg every 4 weeks. This treatment regimen, for example, may be used for treating cancer in a subject wherein the cancer is bladder cancer.

By way of even further example, the compound of Formula I, administered orally at a dose of 100 or 200 mg once daily, may be administered in combination with relatlimab, administered by intravenous infusion at a therapeutically effective dose, in further combination with nivolumab, administered at a dose of 240 mg every 2 weeks, 80 mg every 3 weeks, 360 mg every 3 weeks or 480 mg every 4 weeks. This treatment regiment, for example, may be used for treating cancer in a subject wherein the cancer is an incurable solid malignancy that is metastatic and/or unresectable.

As used herein, "administered to the subject" and similar terms indicate a procedure by which the compound is injected into a patient such that target cells, tissues, or segments of the body of the subject are contacted with the compound. Methods of administration contemplated herein include, but are not limited to, oral, local, inhalation, or parenteral administration. Suitable parenteral methods of administration include, but are not limited to, intravenous, intramuscular, subcutaneous and intradermal parental administration.

The compound of formula I may be in a form suitable for oral use, for example, as as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid;

binding agents, for example, starch, gelatin or acacia, and lubricating agents, for example, magnesium stearate, stearic acid or talc.

In some aspects, a combination of a monoclonal antibody and a compound of Formula I, or a pharmaceutically acceptable salt thereof, as described herein may be administered to a subject with cancer, wherein the subject may have been previously administered at least one prior therapy for the treatment of cancer. Such subjects may be referred to as "treatment experienced" or "non-treatment-naïve." In some aspects, the prior therapy is ongoing. In other aspects, the prior therapy has been discontinued. In these subjects, the prior therapy may have been discontinued for about 12 or 24 hours. In other aspects, the prior therapy may have been discontinued for about 2, 3, 4, 5, or 6 days. In other aspects, the prior therapy may have been discontinued for about 1, 2, 3, 4, 5, 6, 7, or 8 weeks or longer. In some aspects, the prior therapy may have been discontinued for about 3, 4, 5, 6, 7, 8, 9, 10, or about 11 months. In other aspects, the prior therapy may have been discontinued for about 1, 2, 3, 4, 5, 6, 7, 8, 9, or about 10 years.

In some aspects, the cancer is refractory or unresponsive to at least one prior therapy for the treatment of cancer. In a preferred embodiment, the cancer is intravesical bacillus Calumette-Guerin (BCG)-unresponsive non-muscle-invasive bladder cancer (NMIBC). BCG-unresponsive NMIBC is defined as either: (I) BCG refractory, with persistent high-risk NMIBC (CIS, any T1, high-grade Ta) at 6 months despite having received adequate BCG treatment, inclusive of high-grade T1 disease, or any stage or grade progression (stage T1 after initial Ta or CIS, any grade progression to high grade) at the first evaluation approximately 3 months following BCG induction alone; or (II) early relapsing, with recurrence of high-risk NMIBC after achieving a disease-free state, within 6 months of the last treatment of an adequate course of BCG treatment. As used herein, "adequate BGC treatment" is defined as at least 2 courses of BCG, which can include 2 induction courses (at least 5 of 6 weekly doses×2) or 1 induction course (at least 5 of 6 weekly induction doses) and 2 of 3 doses of a maintenance cycle ("5+2").

Examples of the prior therapies include, but are not limited to: surgery, radiotherapy, chemotherapy, immunotherapy, targeted therapy, hormone therapy, stem cell transplant or precision medicine treatment.

As used herein, "chemotherapy" refers to the administration of one or more chemotherapeutic drugs and/or other agents to a cancer patient by various methods, including intravenous, oral, intramuscular, intraperitoneal, intravesical, subcutaneous, transdermal, buccal, inhalation, or in the form of a suppository. In some embodiments, the chemotherapy is platinum-based chemotherapy, for example, platinum-based doublet chemotherapy.

As used herein, "surgery" refers to surgical methods employed to remove cancerous tissue, including but not limited to tumor biopsy or removal of part or all of the colon (colostomy), bladder (cystectomy), spleen (splenectomy), gallbladder (cholecystectomy), stomach (gastrectomy), liver (partial hepatectomy), pancreas (pacreatectomy), ovaries and fallopian tubes (bilateral salpingooophoroectomy),omentum (omentectomy) and /or uterus (hysterectomy).

In some aspects, a combination of a monoclonal antibody and a compound of Formula I, or a pharmaceutically acceptable salt thereof, as described herein may be administered to a subject with cancer, wherein the subject is treatment naïve.

As used herein, "treatment naïve," means that the subject was not previously administered a prior therapy for the treatment of the cancer.

In certain aspects, the monoclonal antibody and a compound of Formula I, or a pharmaceutically acceptable salt thereof, may be administered in further combination with additional therapeutic agents in any manner appropriate under the circumstances. Examples of therapeutic agents that may be used in combinations for treating cancers disclosed herein include radiation, an immunomodulatory agent or chemotherapeutic agent, or diagnostic agent. Suitable immunomodulatory agents that may be used in the present invention include CD40L, B7, and B7RP1; activating monoclonal antibodies (mAbs) to stimulatory receptors, such as, ant-CD40, anti-CD38, anti-ICOS, and 4-IBB ligand; dendritic cell antigen loading (in vitro or in vivo); anti-cancer vaccines such as dendritic cell cancer vaccines; cytokines/chemokines, such as, IL1, IL2, IL12, IL18, ELC/CCL19, SLC/CCL21, MCP-1, IL-4, IL-18, TNF, IL-15, MDC, IFNa/b, M-CSF, IL-3, GM-CSF, IL-13, and anti-IL-10; bacterial lipopolysaccharides (LPS); immune-stimulatory oligonucleotides; and intravesical bacillus Calmette-Geurin (BCG).

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil;

gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, leuprolide, and goserelin; and pharmaceutically acceptable salts, acids or derivatives of any of the above. In certain embodiments, combination therapy comprises administration of a hormone or related hormonal agent.

Chemotherapeutic agents also include signal transduction inhibitors (STI). The term "signal transduction inhibitor" refers to an agent that selectively inhibits one or more steps in a signaling pathway. Signal transduction inhibitors (STIs) of the present invention include: (i) bcr/abl kinase inhibitors (e.g., GLEEVEC™); (ii) epidermal growth factor (EGF) receptor inhibitors, including kinase inhibitors and antibodies; (iii) her-2/neu receptor inhibitors (e.g., HERCEPTIN™); (iv) inhibitors of Akt family kinases or the Akt pathway (e.g., rapamycin); (v) cell cycle kinase inhibitors (e.g., flavopiridol); and (vi) phosphatidyl inositol kinase inhibitors.

In a preferred embodiment, one or more chemotherapeutic agents are administered in combination with the compound of Formula I and, optionally, nivolumab or ipilimumab, or a combination thereof.

Additional treatment modalities that may be used in combination with a monoclonal antibody and a compound of Formula I, or a pharmaceutically acceptable salt thereof, include a cytokine or cytokine antagonist, such as IL-12, IFN, or anti-epidermal growth factor receptor, radiotherapy, a monoclonal antibody against another tumor antigen, a complex of a monoclonal antibody and toxin, a T-cell adjuvant, bone marrow transplant, or antigen presenting cells (e.g., dendritic cell therapy). Vaccines (e.g., as a soluble protein or as a nucleic acid encoding the protein) are also provided herein.

In some aspects, the cancer is a malignant solid tumor. In some aspects, the cancer is a liquid tumor. Examples of the cancers that may be treated using the compounds and compositions described herein include, but are not limited to: non-small cell lung cancer (NSCLC), renal cell carcinoma; squamous cell carcinoma of the head and neck (SCCHN), bladder cancer (including muscle-invasive bladder cancer and non-muscle-invasive bladder cancer), pancreatic cancer, cancers of the prostate, cervix, colorectum, stomach, endometrium, brain, liver, ovary, testis, head, neck, skin (including melanoma and basal carcinoma), mesothelial lining, white blood cell (including lymphoma such as diffuse large B-cell lymphoma and leukemia) esophagus, breast, muscle, connective tissue, lung (including small-cell lung carcinoma and non-small-cell carcinoma), adrenal gland, thyroid, kidney, or bone; glioblastoma, mesothelioma, gastric cancer, sarcoma, choriocarcinoma, cutaneous basocellular carcinoma, and testicular seminoma. In some embodiments, the breast cancer is triple negative breast cancer (TNBC). In preferred aspects, the cancer is cervical cancer, diffuse large B-cell lymphoma, non-small cell lung cancer, renal cell carcinoma; squamous cell carcinoma of the head and neck, bladder cancer, pancreatic cancer, melanoma, lymphoma or gastric cancer. In more preferred aspects, the cancer is melanoma, non-small cell lung cancer, squamous cell carcinoma of the head and neck, bladder cancer, renal cell carcinoma, cervical cancer or gastric carcinoma. In other preferred aspects, the cancer is lymphoma.

In some aspects, the cancers listed herein are advanced or have spread. Cancers that are advanced or have spread include metastatic, unresectable, recurrent, or stage IV cancers, or any combination thereof. Preferred examples of cancers that are advanced or have spread include: stage IV NSCLC, recurrent NSCLC, metastatic SCCHN, recurrent SCCHN, metastatic melanoma, metastatic NSCLC, bladder cancer and cervical cancer. In some aspects, cancer is a brain metastasis from melanoma or NSCLC.

In some aspects of the disclosure, the subject exhibits an improvement in his/her Eastern Cooperative Oncology Group (ECOG) Performance Status following treatment according to any of the disclosed methods. In some aspects, the subject exhibits an ECOG Performance Status of less than or equal to 1 following treatment as described herein. In other aspects, subject exhibits an ECOG Performance Status of less than or equal to 2 following treatment. In other aspects, subject exhibits an ECOG Performance Status of less than or equal to 3 following treatment. In other aspects, subject exhibits an ECOG Performance Status of less than or equal to 4 following treatment. ECOG Performance Status, developed by the Eastern Cooperative Oncology Group, provides the following status descriptions per grade: Grade 0 is fully active, able to carry on all pre-disease performance without restriction; Grade 1 is restricted in physically strenuous activity but ambulatory and able to carry out work of a light or sedentary nature, e.g., light house work, office work; Grade 3 is ambulatory and capable of all self-care but unable to carry out any work activities; up and about more than 50% of waking hours.

In preferred aspects, the pharmaceutically acceptable salt for administering to a subject with cancer is the MSA salt, that is:

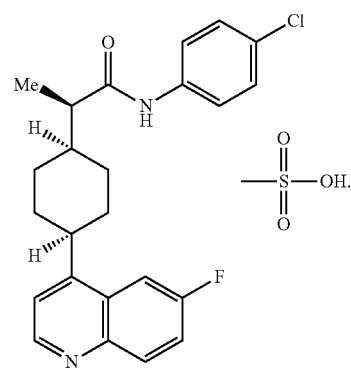

In other aspects, the compound administered is the free base of (R)-N-(4-chlorophenyl)-2-(cis-4-(6-fluoroquinolin-4-yl)cyclohexyl)propanamide.

In some aspects, the subject is an adult. For example, adult populations may include subjects aged 18 and older. In other aspects, the subject is a geriatric subject. For example, geriatric populations may include subjects aged 64 and older. In other aspects, the subject is a pediatric subject. For example, pediatric subjects may be preterm neonatal (the period at birth when a newborn is born before the full gestational period), term neonatal (birth to 27 days), an infant (28 days to 12 months), a toddler (13 months to 2 years), in early childhood (2 years to 5 years), in middle childhood (6 years to 11 years), in early adolescence (12 years to 18 years), or in late adolescence (19 years to 21 years).

In some aspects, the methods of treatment disclosed herein may result in a treatment related adverse event (TRAE) as established by the Common Terminology Criteria for Adverse Events (CTCAE), published by the U.S. Department of Health and Human Services. An Adverse Events (AE) is any unfavorable and unintended sign (including an abnormal laboratory finding), symptom, or disease temporally associated with the use of a medical treatment or procedure that may or may not be considered related to the medical treatment or procedure. An AE is a term that is a unique representation of a specific event used for medical documentation and scientific analyses. The general guidelines as established by the CTCAE are as follows: Grade refers to the severity of the AE where grade 1 is defined as mild; asymptomatic or mild symptoms; clinical or diagnostic observations only; intervention not indicated. Grade 2 is defined as moderate; minimal, local or noninvasive intervention indicated; limiting age-appropriate instrumental activities of daily living (ADL). Grade 3 is severe or medically significant but not immediately life threatening; hospitalization or prolongation of hospitalization indicated; disabling; limiting self-care ADL. Grade 4 is life-threatening consequences; urgent intervention indicated. Grade 5 is death related to AE. Examples of TRAE's greater than or equal to 2 include uveitis, decreased appetite, pyrexia, anemia, autoimmune hepatitis, fatigue, headache, nausea and/or vomiting. Examples of Grade 3/4 TRAEs, also referred to as "serious TRAEs" include increase lipase, hypophosphatemia, rash, increased aspartate aminotransferase, increased alanine aminotransferase, hepatitis, hypertension, pancreatitis, and/or autoimmune hepatitis.

In certain aspects, the treatments described herein may not result in a grade 4 or grade 5 adverse event. In other aspects, the treatments described herein may result in no more than a grade 1 adverse event. In further aspects, the treatments described herein may result in no more than a grade 2 adverse event. In still further aspects, the treatments described herein may result in no more than a grade 3 adverse event.

In aspects of the methods disclosed herein, the subject may exhibit improved anti-tumor activity as measured by objective response rate (ORR), duration of response, and progression-free survival (PFS) rate.

The objective response rate (ORR) may be quantified by an investigator and/or physician to assess response using Response Evaluation Criteria In Solid Tumors (RECIST) v1.1, as developed by a collaboration between the European Organization for Research and Treatment of Cancer (EORTC), the National Cancer Institute (NCI), and the United States and the National Cancer Institute of Canada Clinical Trials Group. Optionally, the ORR may optionally be reviewed by a central imaging lab.

"Progression free survival (PFS)," as used in the context of the cancers described herein, refers to the length of time during and after treatment of the cancer until objective tumor progression or death. The treatment may be assessed by objective or subjective parameters; including the results of a physical examination, neurological examination, or psychiatric evaluation. In preferred aspects, PFS may be assessed by blinded imaging central review and may further optionally be confirmed by ORR or by blinded independent central review (BICR).

The following examples are merely illustrative and are not intended to limit the disclosure to the materials, conditions, or process parameters set forth therein.

EXAMPLES

Example 1. Compound of Formula I Administered in Combination with Nivolumab in Advanced Malignant Tumors A non-limiting example of a clinical trial in cancers that are advanced or have spread involving the combination of a compound of Formula I, or pharmaceutically acceptable salts thereof, and nivolumab is described below.

Purpose: The purpose of this study is to, among other things, assess the safety and tolerability for the combination therapy of the compound of Formula I, or a pharmaceutically acceptable salt thereof, and nivolumab in patients with advanced tumors.

Intervention: Patients are administered a compound of Formula I at a specified dose at specified intervals. In some embodiments, the patients will also be administered a second therapeutic agent in addition to a compound of Formula I. In some embodiments, the second therapeutic agent is nivolumab, which is administered at specified intervals.

Primary Outcome Measures:
Incidence of adverse events with time frame of 15 months.
Incidence of serious adverse events with a time frame of 15 months.
Incidence of death with a time frame of 15 months.
Incidence of laboratory abnormalities with a time frame of 15 months.
Adverse events leading to discontinuation, with a time frame of up to one year.

Secondary Outcome Measures:
Maximum observed plasma concentration (C max) to characterize the Pharmacokinetics (PK) of the compound of Formula I administered alone and in combination with nivolumab. The time frame is up to one year.
Time of maximum observed plasma concentration (T max) to characterize the PK of the compound of Formula I administered alone and in combination with nivolumab. The time frame is up to one year.
Area under the plasma concentration-time curve in one dosing interval [AUC(TAU)] to characterize the PK of the compound of Formula I administered alone and in combination with nivolumab. The time frame is up to one year.
Trough observed plasma concentration at the end of the dosing interval (Ctrough) to characterize the PK of the compound of Formula I administered alone and in combination with nivolumab. The time frame is up to one year.
Apparent total body clearance (CLT/F) to characterize the PK of the compound of Formula I administered alone and in combination with nivolumab. The time frame is up to one year.
Apparent volume of distribution at steady-state (Vss/F) to characterize the PK of the compound of Formula I administered alone and in combination with nivolumab. The time frame is up to one year.

Percent urinary recovery over 24 hours (% UR24) to characterize the PK of the compound of Formula I administered alone and in combination with nivolumab. The time frame is up to 24 hours.

Biomarker Availability to characterize the pharmacodynamic activity of the compound of Formula I administered alone and in combination with nivolumab. The time frame is up to one year.

Incidence of anti-drug antibody (ADA) to characterize the immunogenicity of nivolumab when administered in combination with the compound of Formula I. The time frame is up to one year.

Best Overall Response (BOR) to investigate the preliminary anti-tumor activity of the compound of Formula I when administered in combination with nivolumab in advanced malignant tumors. The time frame is up to one year.

Duration of Response (DOR) to investigate the preliminary anti-tumor activity of the compound of Formula I when administered in combination with nivolumab in advanced malignant tumors. The time frame is up to one year.

Experimental Treatment Arm

Monotherapy and Combination Therapy (Dose Escalation): participants received a compound of Formula I plus nivolumab at specified doses at specified intervals.

Eligibility

Inclusion Criteria (study open to all sexes, 20 years and older):

Participants must have histologic or cytological confirmation of a malignancy that is advanced (metastatic and/or unresectable) with measureable disease per Response Evaluation Criteria In Solid Tumors (RECIST v1.1).

Participants must have received, and then progressed or been intolerant to standard treatment regimen in the advanced or metastatic setting.

Eastern Cooperative Oncology Group performance status of ≤1.

Exclusion Criteria:

Participants with known or suspected CNS metastases, untreated CNS metastases, or with the CNS as the only site of disease are excluded.

History of congenital or autoimmune hemolytic disorders.

History or presence of hypersensitivity or idiosyncratic reaction to methylene blue.

Example 2. Compound of Formula I Administered in Combination with Nivolumab and in Combination with Both Nivolumab and Ipilimumab in Advanced Malignant Tumors A non-limiting example of a clinical trial in cancers that are advanced or have spread involving the combination of a compound of Formula I, or pharmaceutically acceptable salts thereof, and nivolumab and the combination of a compound of Formula I, or pharmaceutically acceptable salts thereof, and nivolumab and ipilimumab is described below.

Purpose: The purpose of the study is to, among other things, determine safety and effectiveness of a compound of Formula I (or salt thereof) when combined with nivolumab and in combination with both nivolumab and ipilimumab in patients with cancers that are advanced or have spread. Pharmacokinetics and pharmacodynamics (including immunomodulatory assays) of a compound of Formula I when combined with nivolumab and in combination with nivolumab and ipilimumab in this patient population will also be assessed.

Intervention: Patients are administered a compound of Formula I at a specified dose at specified intervals. The patients will be administered a second therapeutic agent in addition to a compound of Formula I. In some embodiments, the second therapeutic agent is nivolumab, which is administered at specified intervals. Some patients will also be administered a third therapeutic agent in addition to a compound of Formula I and nivolumab. In some embodiments, the third therapeutic agent is ipilimumab, which is administered at specified intervals.

Primary Outcome Measures:

Safety and tolerability of a compound of Formula I as measured by a composite of the incidence of adverse events (AEs), serious adverse events (SAEs), AEs leading to discontinuation, deaths, and clinical laboratory test abnormalities. The time frame is 100 days after the last dose of study therapy.

Safety of a compound of Formula I plus nivolumab as measured by a composite of the incidence of adverse events (AEs), serious adverse events (SAEs), AEs leading to discontinuation, deaths, and clinical laboratory test abnormalities. The time frame is 100 days after the last dose of study therapy.

Safety of a compound of Formula I plus both nivolumab and ipilimumab as measured by incidence of adverse events (AEs), serious adverse events (SAEs), AEs leading to discontinuation, deaths, and clinical laboratory test abnormalities. The time frame is 100 days after the last dose of study therapy.

Anti-tumor activity of a compound of Formula I administered in combination with nivolumab as measured by the best overall response (BOR) as measured by CT scan. The time frame is approximately 3 years.

Anti-tumor activity of a compound of Formula I administered in combination with nivolumab as measured by the duration of response (DOR) as measured by CT scan. The time frame is approximately 3 years.

Anti-tumor activity of a compound of Formula I administered in combination with nivolumab as measured by progression-free survival rates (PFSRs) as measured by CT scan. The time frame is approximately 3 years.

Anti-tumor activity of a compound of Formula I administered in combination with both nivolumab and ipilimumab as measured by the best overall response (BOR) as measured by CT scan. The time frame is approximately 3 years.

Anti-tumor activity of a compound of Formula I administered in combination with both nivolumab and ipilimumab as measured by the duration of response (DOR) as measured by CT scan. The time frame is approximately 3 years.

Anti-tumor activity of a compound of Formula I administered in combination with both nivolumab and ipilimumab as measured by progression-free survival rates (PFSRs) as measured by CT scan. The time frame is approximately 3 years.

Secondary Outcome Measures

Maximum observed plasma concentration (C max) of a compound of Formula I as measured by plasma concentration with a time frame of approximately 3 years.

Time of maximum observed plasma concentration (T max) of a compound of Formula I as measured by plasma concentration with a time frame of approximately 3 years.

Area under the concentration-time curve from time zero extrapolated to infinite time [AUC(INF)] of a compound of Formula I as measured by plasma concentration with a time frame of approximately 3 years.

Area under the concentration-time curve from time zero to the time of the last quantifiable concentration [AUC (0-T)] of a compound of Formula I as measured by plasma concentration with a time frame of approximately 3 years.

Area under the concentration-time curve in 1 dosing interval [AUC(TAU)] of a compound of Formula I as measured by plasma concentration with a time frame of approximately 3 years.

Trough observed plasma concentration at the end of the dosing interval (Ctrough) of a compound of Formula I as measured by plasma concentration with a time frame of approximately 3 years.

Observed plasma concentration at 24 hours (C24) of a compound of Formula I as measured by plasma concentration with a time frame of approximately 3 years.

Apparent terminal phase half-life (T-HALF) of a compound of Formula I as measured by plasma concentration with a time frame of approximately 3 years.

Apparent total body clearance (CLT/F) of a compound of Formula I as measured by plasma concentration with a time frame of approximately 3 years.

Apparent renal clearance (CLR/F) of a compound of Formula I as measured by plasma concentration with a time frame of approximately 3 years.

Volume of distribution of terminal phase (Vz/F) of a compound of Formula I as measured by plasma concentration with a time frame of approximately 3 years.

Apparent volume of distribution at steady state (Vss/F) of a compound of Formula I as measured by plasma concentration with a time frame of approximately 3 years.

Accumulation index (AI) of a compound of Formula I as measured by plasma concentration with a time frame of approximately 3 years.

Percent urinary recovery (% UR) of a compound of Formula I as measured by urine concentration with a time frame of approximately 3 years.

Percent urinary recovery over 24 hours (% UR24) of a compound of Formula I as measured by urine concentration with a time frame of approximately 3 years.

Ratio of metabolite C max to parent C max, corrected for molecular weight (MR_C max) of a compound of Formula I as measured by plasma concentration with a time frame of approximately 3 years.

Ratio of metabolite AUC(0-T) to parent AUC(0-T), corrected for molecular weight (single dose in clinical pharmacology substudy only) [MR_AUC(0-T)] of a compound of Formula I as measured by plasma concentration with a time frame of approximately 3 years.

Ratio of metabolite AUC(TAU) to parent AUC(TAU), corrected for molecular weight [MR_AUC(TAU)] of a compound of Formula I as measured by plasma concentration with a time frame of approximately 3 years.

Ratio of metabolite AUC(INF) to parent AUC(INF), corrected for molecular weight (single dose in clinical pharmacology substudy only) [MR_AUC(INF)] of a compound of Formula I as measured by plasma concentration with a time frame of approximately 3 years.

Anti-drug antibody (ADA) response to nivolumab in combination with a compound of Formula I as measured by immunoassay and liquid chromatography-mass spectrometry with a time frame of approximately 3 years.

Anti-drug antibody (ADA) response to ipilimumab in combination with a compound of Formula I as measured by immunoassay and liquid chromatography-mass spectrometry with a time frame of approximately 3 years.

Experimental Treatment Arms

1. Combination Therapy (Dose Escalation). Participants with advanced cancers received a compound of Formula I orally (PO), daily (QD) at a dose of 25 mg, 50 mg, 100 mg or 200 mg for all advanced cancers over a 2 week lead-in period. Participants were then also administered nivolumab intravenously at a dose of 240 mg once every two weeks.

2. Combination Therapy (Dose Expansion). A total of 219 participants with select previously treated advanced malignancies received a compound of Formula I at a dose of 100 or 200 mg orally once daily plus nivolumab at a dose of 240 mg intravenously once every two weeks (Q2W) or at a dose of 480 mg intravenously once every four weeks (Q4W). Advanced malignancies included cervical cancer (21 patients), diffuse large B-cell lymphoma (DLBCL) (4 patients), non-small cell lung cancer (NSCLC) (7 patients), renal cell carcinoma (RCC) (0 patients); squamous cell carcinoma of the head and neck (SCCHN) (16 patients), bladder cancer (18 patients), pancreatic cancer (18 patients), melanoma (21 patients), and ASST, a mixed tumor type cohort consisting of sarcoma, endometrial and breast cancer (19 patients). Out of a total of 219 participants, 174 received prior surgery, 129 received prior radiotherapy, 202 received prior system therapy, including 24 with prior treatment with an anti-PD-L(1) inhibitor. IDO1 inhibitor therapy is not permitted. Prior exposure to immune checkpoint inhibitors or therapy targeting T-cell costimulation requires a washout period of >4 weeks.

3. Combination Therapy 2 (Dose Expansion). Participants with advanced cancers received a compound of Formula I plus both nivolumab and ipilimumab at specified doses at specified intervals.

Eligibility

Inclusion Criteria (study open to all sexes, 18 years to 100 years):

During dose escalation, subjects with advanced solid tumors that have progressed following at least one standard regimen.

During cohort expansion, subjects with advanced cancer that either have received at least one prior therapy or are treatment naive, depending on the specified tumor type.

Subjects must have measurable disease.

Subject must consent to provide previously collected tumor tissue and a tumor biopsy during screening.

At least 4 weeks since any previous treatment for cancer.

Must be able to swallow pills or capsules.

Eastern Cooperative Oncology Group (ECOG) Performance Status 0-1.

Exclusion Criteria:

Active or chronic autoimmune diseases.

Uncontrolled or significant cardiovascular disease.

History of any chronic Hepatitis, active Hepatitis B or C, human immunodeficiency virus (HIV), or acquired immune deficiency syndrome (AIDS).

Chronic hepatitis: Positive test for Hepatitis B virus surface antigen or Hepatitis C antibody (except for subjects with hepatocellular carcinoma).

Active central nervous system (CNS) metastases and CNS metastases as the only sites of disease.

Active infection.

Results: Safety data was available for 216 patients across the study. Maximum tolerated dose during escalation was 200 mg; at 400 mg, 2/4 patients experienced dose-limiting toxicities (grade 3 AST/ALT; grade 2 anemia, fatigue). The dose escalation phase results are summarized in Table 1.

TABLE 1

Dose escalation final results

| | 25 mg | 50 mg | 100 mg | 200 mg | 400 mg |
|---|---|---|---|---|---|
| # of DLTs[1]/ # DLT evaluable | 0/7 | 0/8 | 1/9 | 3/12 | 2/4 |
| DLTs | | | Grade 3 autoimmune hepatitis | 1. Grade 3 fatigue and Grade 3 anemia leading to dose reduction 2. Grade 3 AST[2] and ALT[3] elevations 3. Grade 3 anemia leading to dose reduction | 1. Grade 3 AST and ALT elevations 2. Grade 2 fatigue and anemia leading to >25% of compound of Formula I doses missed and requiring dose reduction |

[1]DLT = dose limiting toxicity
[2]AST = aspartate aminotransferase
[3]ALT = alanine aminotransferase Treatment-related adverse events occurred in 47% of patients (11% grade 3/4), and 4 patients (2%) discontinued due to study drug toxicity. The safety profile was generally consistent with that reported for nivolumab monotherapy (Siu L, et al. *AACR* 2017). In the bladder cancer cohort, among 15 heavily pretreated patients (39% received ≥2 prior regimens), 5 partial responses (PRs), 3 stable disease (SD), and 6 progressive disease (PD, including a patient with prior anti-PD-[L]1 therapy) were reported, with 1 death prior to assessment. In the cervical cancer cohort, among 17 heavily pretreated patients (52% received ≥2 prior regimens), 3 PRs, 5 SD, and 7 PD were reported, with 2 deaths prior to assessment. The observed responses to treatment with the compound of Formula I and nivolumab are summarized in Table 2.

Antitumor activity was observed in patients with advanced cervical or bladder cancer. As illustrated in Table 3, below, an objective response rate (ORR) of 14% and a disease control rate (DCR) of 64% were observed in heavily pre-treated advanced cervical cancer. Additionally, an ORR of 32% and a DCR of 44% were observed in advanced bladder cancer.

TABLE 3

Antitumor activity in patients with advanced cervical or bladder cancer

| | All Evaluable Cervical Cancer Patients[a] | All Evaluable Bladder Cancer Patients[a] |
|---|---|---|
| Patients, n | 20 | 24 |
| Patients, n (%) | | |
| Complete response | 0 | 0 |
| Partial response | 3 (13.6)[b] | 8 (32.0)[c] |
| Stable disease | 11 (50.0) | 3 (12.0) |
| Progression disease | 6 (27.3) | 13 (52.0) |
| Objective response rate[d], % (95% Cl) | 3 (13.6) (2.9, 34.9) | 8 (32.0) (14.9, 53.5) |
| Disease control rate[e], % (95% Cl) | 14 (63.6) (40.7, 82.8) | 11 (44.0) (24.4, 65.11) |
| Median duration of therapy, weeks (95% Cl) | 13.3 (2-32) | 8.0 (2-41) |

[a]Includes all patients how have at least 1 reported on-treatment tumor assessment.
[b]1 patient had a confirmed partial response.
[c]7 patients (28%) had a confirmed partial response.
[d]Complete responses plus partial responses.
[e]Complete responses plus partial responses plus stable disease.

Figure 1B:
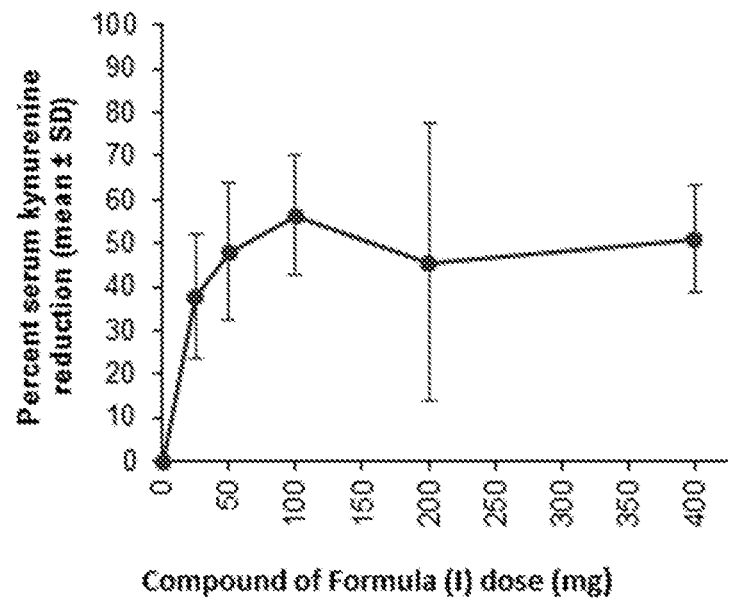
FIG. 1B illustrates percent serum kynurenine reduction at 20 mg, 50 mg, 100 mg, 200 mg or 400 mg of the compound of Formula (I).

As depicted in FIG. 1A, within 39 paired pre- vs on-treatment tumor samples across various tumor types, intratumoral kynurenine was reduced across all doses following treatment, including in samples with relatively high pretreatment kynurenine levels. Dark bars represent a pretreatment kynurenine condition and light bars represent an on-treatment kynurenine (C1D15) condition. Asterisks (*) denotes samples below the lower limit of quantitation. FIG. 1B demonstrates approximately a 60% reduction in serum kynurenine levels with administration of the compound of Formula (I) at a dose of 100 mg once daily.

Figure 2:
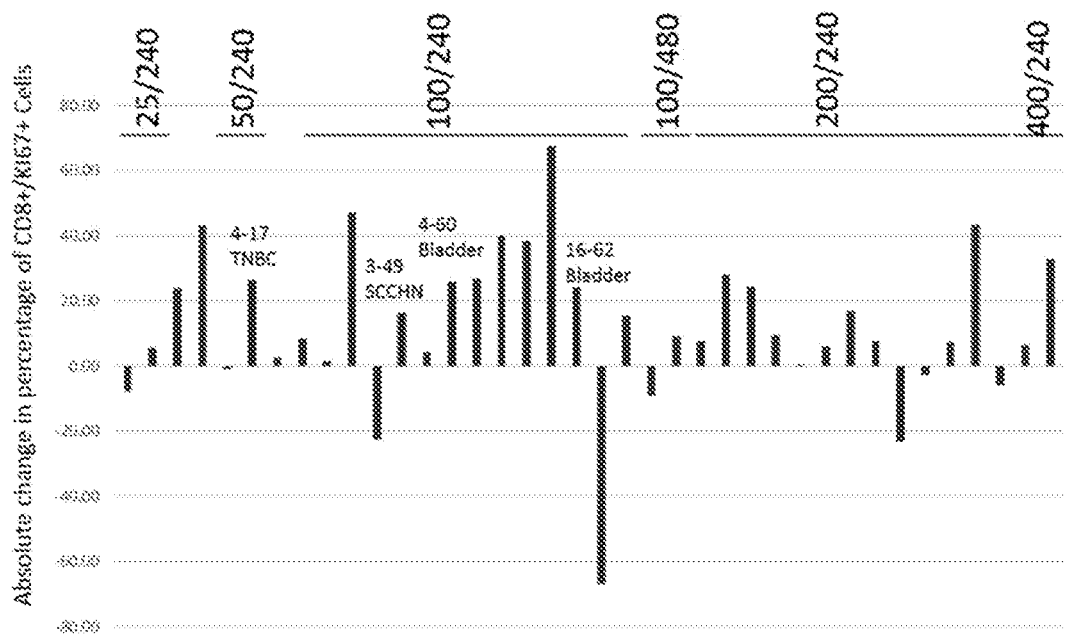
FIG. 2 illustrates biomarker analyses of tumor samples pre- and on-treatment using an embodiment of the disclosure.

As depicted in FIG. 2, within 39 paired pre- vs on-treatment tumor samples across various tumor types, the compound of Formula (I) plus nivolumab increased the percentage of Ki67+/CD8+ T cells. Partial response (PR) conditions are marked above the corresponding data bar

TABLE 2

Response to treatment with the compound of Formula I and nivolumab

| Compound of Formula I + Nivolumab | Cerv n = 21 n (%) | Panc n = 18 n (%) | DLBCL n = 4 n (%) | SCCHN n = 16 n (%) | Bladder n = 18 n (%) | MEL n = 21 | NSCLC n = 19 | ASST n = 19 |
|---|---|---|---|---|---|---|---|---|
| Not evaluable | 4 | 5 | 4 | 7 | 3 | 16 | 18 | 12 |
| Evaluable | | | | | | | | |
| PR | 3 (18) | 0 | 0 | 2 (22) | 5 (33) | 2 (40) | 0 | 0 |
| SD | 5 (29) | 0 | 0 | 2 (22) | 3 (20) | 0 | 0 | 2 (29) |
| PD | 7 (41) | 11 (85) | 0 | 2 (22) | 6 (40) | 3 (60) | 1 (100) | 5 (71) |
| Death | 2 (12) | 2 (15) | 0 | 3 (33) | 1 (7) | 0 | 0 | 0 |

Figure 3:
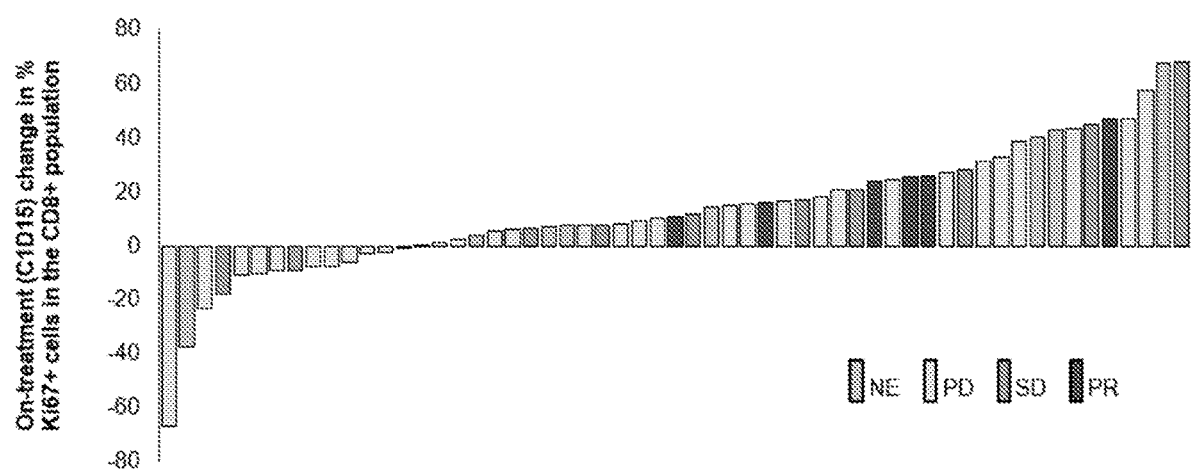
FIG. 3 illustrates biomarker analyses of tumor samples on-treatment using an embodiment of the disclosure.
Figure 4A:
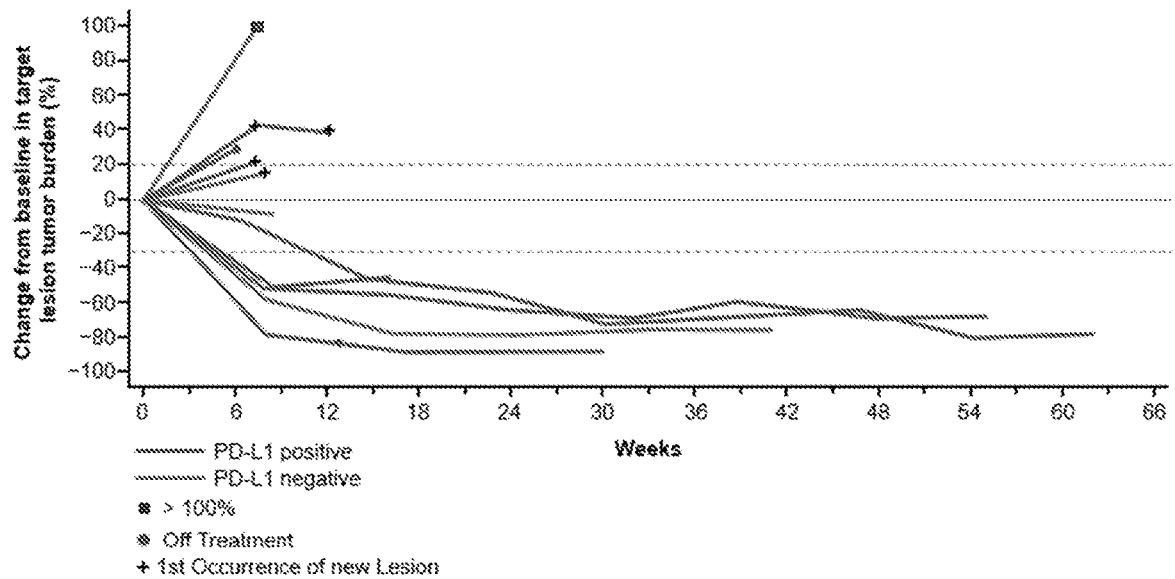
FIG. 4A illustrates change from baseline in target lesion tumor burden (%) over time for PD-L1 positive and PD-L1 negative advanced bladder cancer patients administered 100 mg of the compound of Formula (I) plus nivolumab.
Figure 4B:
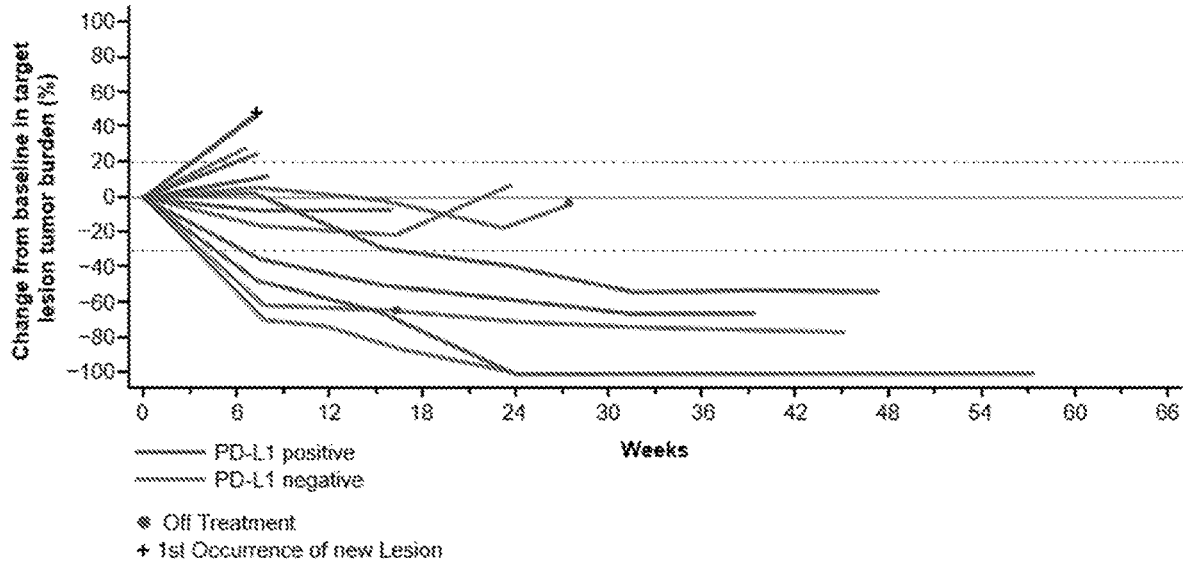
FIG. 4B illustrates change from baseline in target lesion tumor burden (%) over time for PD-L1 positive and PD-L1 negative advanced bladder cancer patients administered 200 mg of the compound of Formula (I) plus nivolumab.
Figure 5A:
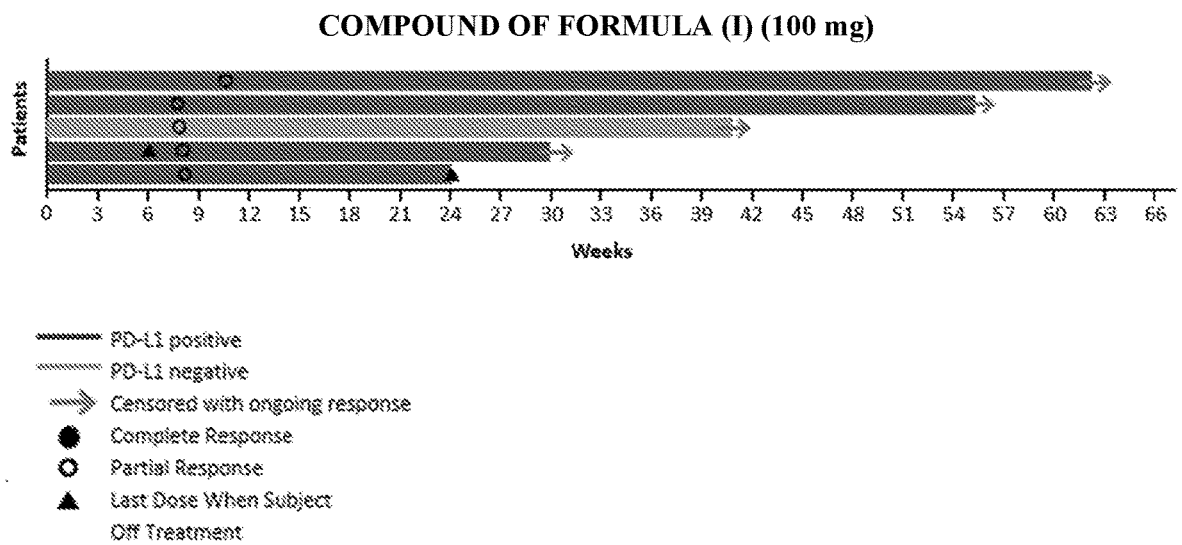
FIG. 5A illustrates time to and duration of response in advanced bladder cancer patients with IL-naïve advanced bladder cancer who responded to 100 mg of the compound of Formula (I) plus nivolumab.
Figure 5B:
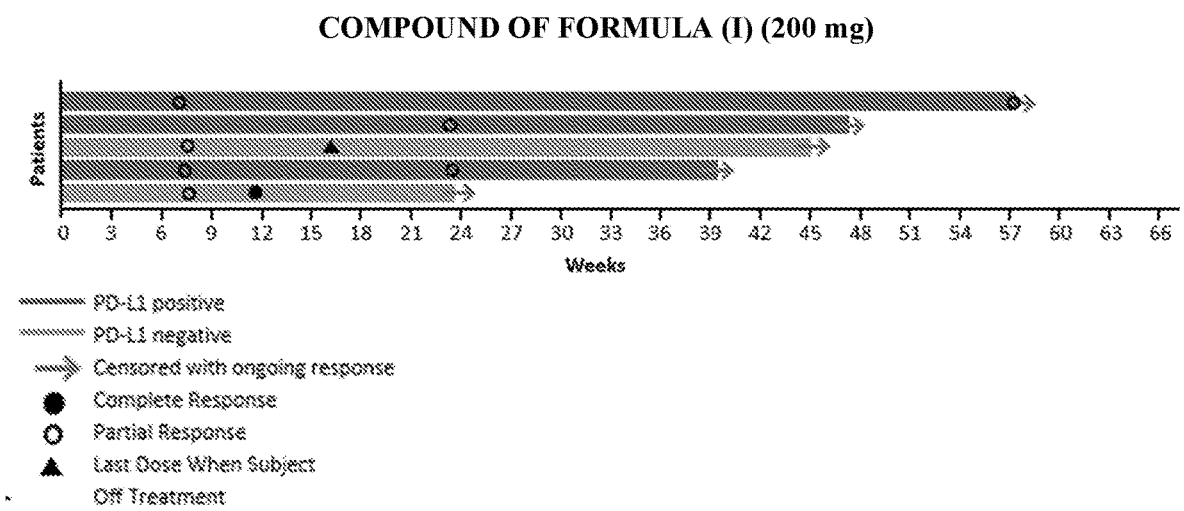
FIG. 5B illustrates time to and duration of response in advanced bladder cancer patients with IL-naïve advanced bladder cancer who responded to 200 mg of the compound of Formula (I) plus nivolumab.

[a]Includes subjects who have not yet reached fir imaging assessment and those without imaging data available/investigator-reported BOR.

with text. FIG. 3 shows, for on-treatment tumor samples marked as not evaluable (NE), progressive death (PD), stable disease (SD) and partial response (PR) conditions, the compound of Formula (I) plus nivolumab increased the percentage of Ki67+/CD8+ T cells.

Conclusions

The compound of Formula I plus nivolumab was well-tolerated, increased proliferating CD8+ T cells in tumors, and demonstrated preliminary antitumor efficacy.

Example 3. Compound of Formula I Administered in Combination with Nivolumab in Patients with Advanced Renal Cell Carcinoma A non-limiting example of a clinical trial for patients with advanced renal cell carcinoma involving the combination of a compound of Formula I, or pharmaceutically acceptable salts thereof, and nivolumab in the treatment of advanced renal cell carcinoma is described below.

Intervention: Patients are administered nivolumab at a specified dose at specified intervals. In some embodiments, the patients will also be administered a second therapeutic agent in addition to nivolumab. In some embodiments, the second therapeutic agent is the compound of Formula I, or a salt thereof, which is administered at specified intervals. In some embodiments, the second therapeutic agent is ipilimumab, which is administered at specified intervals.

Primary Outcome Measures:
Objective response rate (ORR) with time frame of up to 24 weeks.
Duration of response (DOR) with a time frame of up to 24 weeks.
Progression-free survival rate (PFSR) with a time frame of up to 24 weeks.
Secondary Outcome Measures:
Safety is measured by incidence of adverse events (AEs) with a time frame of up to 268 days.
Safety is measured by incidence of serious adverse events (SAEs) with a time frame of up to 268 days.
Tolerability is measured by incidence of AEs with a time frame of up to 268 days.
Tolerability is measured by SAEs with a time frame of up to 268 days.
Active Comparator Arm: Nivolumab plus Ipilimumab: participants will receive nivolumab plus ipilimumab at specified doses at specified intervals.
Experimental Treatment Arm: Nivolumab plus a compound of Formula I: participants will receive nivolumab plus a compound of Formula I, or a salt thereof, at specified doses at specified intervals.
Eligibility
Inclusion Criteria (Study Open to All Sexes, 18 Years and Older):
Participants must have advanced renal cell carcinoma.
Participants must have at least 1 lesion with measurable disease.
Participants must have a life expectancy of at least 3 months.
Exclusion Criteria:
Participants with suspected or known central nervous system metastases unless adequately treated.
Participants with autoimmune disease.
Participants who need daily oxygen therapy.

Example 4. Compound of Formula I Administered in Combination with Nivolumab in Patients with Advanced Gastric Cancer A non-limiting example of a clinical trial for patients with advanced gastric cancer involving the combination of a compound of Formula I, or pharmaceutically acceptable salts thereof, and nivolumab is described below.

Intervention: Patients are administered nivolumab at a specified dose at specified intervals. In some embodiments, the patients will also be administered a second therapeutic agent in addition to nivolumab. In some embodiments, the second therapeutic agent is the compound of Formula I, or a salt thereof, which is administered at specified intervals. In some embodiments, the second therapeutic agent is ipilimumab, which is administered at specified intervals.

Primary Outcome Measures:
Objective response rate (ORR) with time frame of up to 24 weeks.
Duration of response (DOR) with a time frame of up to 24 weeks.
Progression-free survival rate (PFSR) with a time frame of up to 24 weeks.
Secondary Outcome Measures:
Incidence of adverse events (AEs) with a time frame of up to 38 weeks.
Incidence of serious adverse events (SAEs) with a time frame of up to 38 weeks.
AEs leading to discontinuation with a time frame of up to 38 weeks.
AEs leading to death with a time frame of up to 38 weeks.
Study Arms:
Active Comparator Arm: Nivolumab plus Ipilimumab: participants will receive nivolumab plus ipilimumab at specified doses at specified intervals.
Experimental Treatment Arm: Nivolumab plus a compound of Formula I: participants will receive nivolumab plus a compound of Formula I, or salt thereof, at specified doses at specified intervals.
Eligibility:
Inclusion Criteria (Study Open to All Sexes, 18 Years and Older):
Participants must have advanced gastric cancer.
Participants must have at least 1 lesion with measurable disease.
Participants must have full activity or, if limited, must be able to walk and carry out light activities such as light house work or office work.
Exclusion Criteria:
Participants with HER2 positive tumor that has not been treated with trastuzumab prior to enrollment.
Participants with suspected or known central nervous system metastases unless adequately treated.
Participants with autoimmune disease.
Participants who need daily oxygen therapy.

Example 5. Compound of Formula I Administered in Combination with Nivolumab with or Without Chemotherapy in Patients with Previously Untreated Stage IV or Recurrent Non-Small Cell Lung Cancer (NSCLC)

A non-limiting example of a clinical trial for patients with previously untreated stage IV or recurrent non-small cell lung cancer involving the combination of a compound of Formula I, or pharmaceutically acceptable salts thereof, and nivolumab with our without chemotherapy is described below.

Intervention: Patients are administered nivolumab at a specified dose at specified intervals in combination with the compound of Formula I, administered orally at 100 mg daily. In some embodiments, the patients will also be administered platinum-based doublet chemotherapy in addition to nivolumab and the compound of Formula I. In other embodiments, the patients are administered platinum-based doublet chemotherapy alone without nivolumab or the compound of Formula I.

Primary Outcome Measures:

Objective response rate (ORR) measured by number of participants with a best overall response (BOR) of confirmed complete response (CR) or partial response (PR) divided by the number of randomized participants for each treatment group with time frame of up to 24 weeks.

Progression-free survival (PFS) measured by the time between the date of randomization and the first date of documented progression, as determined by the Blinded Independent Central Review, or death, due to any cause, whichever occurs first with a time frame of up to 24 weeks.

Secondary Outcome Measures:

Overall survival (OS) measured by the time between the date of randomization and the date of death due to any cause, with a time frame of approximately 5 years.

Number of treatment-related adverse events (AE) with a time frame of approximately 5 years.

Number of treatment-related serious adverse events with a time frame of approximately 5 years.

Study Arms:

Active Comparator Arm: Chemotherapy administered alone. Participants will receive platinum-based doublet chemotherapy following standard administration regimens.

Experimental Treatment Arm A: Nivolumab plus a compound of Formula I. Participants will receive nivolumab at specified doses at specified intervals plus a compound of Formula I, or salt thereof, at a dose of 100 mg orally once daily.

Experimental Treatment Arm B: Nivolumab plus a compound of Formula I plus chemotherapy. Participants will receive nivolumab at specified doses at specified intervals plus a compound of Formula I, or salt thereof, at a dose of 100 mg orally once daily plus platinum-based doublet chemotherapy following standard administration regimens.

Eligibility

Inclusion Criteria (Study Open to All Sexes, 18 Years and Older):

Participants must have histologically confirmed stage IV NSCLC per the 8th IASLC of squamous or non-squamous histology.

Participants must have locally advanced disease with recurrence after chemoradiation therapy (stage IIIB disease, specifically refers to patients with no curative treatment options).

Participants must have no prior systemic anti-cancer therapy (including EGFR and ALK/ROS1 inhibitors) given as primary therapy for advanced or metastatic disease.

Participants must have biomarker test results available for randomization.

Participants must have an Eastern Cooperative Oncology Group (ECOG) Performance Status of ≤1.

Participants must have measurable disease by CT or MRI per RECIST 1.1 criteria.

Exclusion Criteria:

Participants with known sensitizing EGFR mutations or known ALK/ROS1 rearrangements.

Participants with interstitial lung disease that is symptomatic or may interfere with the detection or management of suspected drug-related pulmonary toxicity.

Participants with an active, known or suspected autoimmune disease (participants with type I diabetes mellitus, hypothyroidism only requiring hormone replacement, skin disorders (such as vitiligo, psoriasis, or alopecia) not requiring systemic treatment, or conditions not expected to recur in the absence of an external trigger are permitted to enroll).

Participants with untreated CNS metastases are excluded (participants are eligible if CNS metastases are adequately treated and participants are neurologically returned to baseline (except for residual signs or symptoms related to the CNS treatment) for at least 2 weeks prior to first treatment).

Example 6. Compound of Formula I Administered in Combination with Nivolumab Compared to Standard of Care Regimen in First-Line Recurrent/Metastatic Squamous Cell Carcinoma of the Head and Neck A non-limiting example of a clinical trial for patients with head and neck cancer that has come back after initial treatment, or is widespread when first diagnosed, involving the combination of a compound of Formula I, or pharmaceutically acceptable salts thereof, and nivolumab is described below.

Intervention: Patients are administered nivolumab at a specified dose at specified intervals in combination with the compound of Formula I, administered at 100 mg orally once daily for a maximum of 104 weeks.

Primary Outcome Measures:

Objective response rate (ORR) determined by Blinded Independent Central Review (BICR) using RECIST 1.1 with time frame of approximately 2 years.

Progression-free survival (PFS) determined by BICR using RECIST 1.1 with a time frame of approximately 2 years.

Overall survival (OS) with a time frame of approximately 40 months.

Secondary Outcome Measures:

Number of adverse events (AE) with a time frame of approximately 2 years.

Number of serious adverse events (SAE) with a time frame of approximately 2 years.

Time to meaningful symptomatic deterioration (TTSD) with a time frame of approximately 2 years.

Study Arms:

Active Comparator Arm: Cetuximab plus Cisplatin/Carboplatin plus Fluorouracil: participants will receive Cetuximab at 400 mg/m$^2$ by intravenous administration once only, then 250 mg/m$^2$ weekly maintenance until disease progression, unacceptable toxicity, withdrawal of informed consent or other reason. Participants will also receive Cisplatin at 100 mg/m$^2$ every 3 weeks for up to 6 cycles. Participants will also receive Carboplatin AUC of 5 mg per milliliter per minute every 3 weeks for up to 6 cycles. Finally, participants will also receive Fluorouracil at 1000 mg/m$^2$ per day for 4 days, ever 3 weeks for up to 6 cycles.

Experimental Treatment Arm A: Nivolumab plus the compound of Formula I: participants will receive nivolumab at specified doses at specified intervals plus a compound of Formula I, or salt thereof, at a dose of 100 mg orally once daily for a maximum of 104 weeks.

Eligibility

Inclusion Criteria (Study Open to All Sexes, 18 Years and Older):
- Participants must have histologically confirmed squamous cell carcinoma of the head and neck (SCCHN), from any of the following primary sites only: oral cavity, oropharynx, hypopharynx, and larynx.
- Participants must have recurrent or metastatic disease that is not amenable to therapy with curative intent (surgery or radiation therapy with or without chemotherapy).
- Participants must have no prior treatment with systemic anti-cancer therapy for SCCHN, unless protocol specified criteria are met.
- Participants must have an ECOG Performance Status of 0-1.
- Participants must have measurable disease by CT or MRI per RECIST 1.1 criteria.

Exclusion Criteria:
- Female participants who are pregnant or breastfeeding.
- Participants with recurrent or metastatic carcinoma of the nasopharynx, squamous cell carcinoma of unknown primary, squamous cell carcinoma that originated from the skin and salivary gland or paranasal sinus, non-squamous histologies (eg, mucosal melanoma).
- Participants with untreated CNS metastases are excluded.
- Participants with carcinomatous meningitis.
- Participants with prior malignancy active within the previous 3 years except for locally curable cancers that have been apparently cured, such as basal or squamous cell skin cancer, superficial bladder cancer, or carcinoma in situ of the prostate, cervix, or breast.

Example 7: Compound of Formula I Administered in Combination with Nivolumab in Patients with Active Brain Metastases from Melanoma and Non-Small Cell Lung Cancer (NSCLC)

A non-limiting example of a Phase II, parallel cohort, single arm clinical trial for patients with active brain metastases from melanoma and NSCLC involving the combination of the compound of Formula I, or pharmaceutically acceptable salts thereof, and nivolumab is described below.

Intervention: Patients are administered nivolumab, administered intravenously at 480 mg every 4 weeks (Q4W), in combination with the compound of Formula I, administered orally at 100 mg daily, for a period of 2 years.

Primary Outcome Measures:
Intracranial objective response rate (IORR) of melanoma or NSCLC brain metastases as measured by modified RECIST 1.1.

Secondary Outcome Measures:
Neurological toxicities and overall safety profile.
Extracranial objective response rate (ORR)
Intracranial and extracranial progression-free survival (PFS) and overall survival (OS) rate and clinical benefit rate with a time frame of 6 months, 12 months, and 2 years.
IORR by response assessment in neuro-oncology brain metastases (RANO-BM) (modified to allow lesions of 5 mm and great) and immunotherapy response assessment for neuro-oncology (iRANO). RANO-BM is measured in at least one dimension, with a minimum size of 10 mm, visible on two or more axial slices. Although the longest diameter in the plane of measurement is recorded, the diameter perpendicular to the longest diameter in the plane of measurement should be at least 5 mm.
Neurocognitive assessments and quality of life (QOL) measures.
Global clinical activity (by ORR and 6 month PFS for measuring intracranial and extracranial response(s)).

Exploratory Outcome Measures
Advanced MRI imaging to evaluate blood flow and necrosis, among other indicators.
Assess available intracranial and/or extracranial tumor tissue obtain at baseline, on treatment, and at time of progression for:
Expression of PD-L1 and IDO in tumor tissue, T-cell receptor next-generation sequencing (TCR NGS) for diversity and clonality, mRNA signature (inflammatory, IPRES), IDO metabolism products, cytokine expression, tumor mutation burden and driver mutations/somatic genomic alterations.
Peripheral blood assays to assess immune cell subsets by flow cytometry, myeloid CD45+/CD11b/PDL1+, PD-1+, Ki67+, CD8+ T cells, TCR NGS for diversity and clonality, IDO metabolism products, cytokine expression and cfDNA.
Cerebrospinal fluid assays to assess for immune cell subsets and cfDNA analysis.

Experimental Treatment Arm: Participants with metastatic melanoma with asymptomatic CNS involvement (n=40) or patients with metastatic NSCLC with asymptomatic CNS involvement (n=40) will receive nivolumab, administered intravenously at 480 mg Q4W, in combination with the compound of Formula I, administered orally at 100 mg daily for 2 years or until POD. Participants will receive a brain MRI after one drug cycle, followed by a brain MRI plus CT scan every 2 cycles up to 12 cycles, and thereafter participants will receive a brain MRI plus CT scan every 3 cycles until PD Eligibility Inclusion Criteria:
Participants must have histologically confirmed metastatic melanoma or NSCLC with asymptomatic brain metastasis.
Participants must have measurable disease defined by at least one untreated and/or progression CNS lesion measuring ≥5 mm-≤3 cm, and at least one measureable CNS lesion that has not been irradiated.
Melanoma participants must be naïve for check-point inhibitor (CPI) therapy in advances cases, though NSCLC participants may have received prior CPI therapy.
Whole brain radiotherapy (WBRT) is permitted for participants with NSCLC.

Exclusion Criteria:
Participants with melanoma having received prior anti-PD-1/PD-L1 or IDO inhibitors in metastatic setting.
Participants with underlying neurological disease (Guillain-Barre, multiple sclerosis, or underlying active seizure disorder).
Participants with NSCLC with EGFR mutations, anaplastic lymphoma kinase (ALK)/c-ros oncogene (ROS) fusions who are eligible for oral tyrosine kinase inhibitor (TKI) therapy.

Statistical Methodology: Continuous monitoring of futility and toxicity will be assessed using Bayesian methods. The proportion of patients experiencing response (i.e., ORR and RR) will be computed with associated 95% confidence intervals. Six-month, twelve-month and two year incracranial and extracranial PFS and OS rate will be determine using the Kaplan-Meier method. Toxicities will be summarized by frequencies and percentages for each cohort.

Example 8: Compound of Formula I in Combination with Nivolumab, or in Further Combination with Intravesical BCG, in Participants with BGC-Unresponsive, High-Risk, Non-Muscle Invasive Bladder Cancer A non-limiting example of a Phase II, randomized, study of the Compound of Formula I in combination with nivolumab, or in further combination with Intravesical BCG, in participants with BGC-unresponsive, high-risk, non-muscle invasive bladder cancer (NMIBC) is described below.

Purpose: The purpose of this study is to, among other things, determine efficacy of nivolumab, alone or in combination with BMS-986205, and with or without intravesical bacillus Calumette-Geurin (BC), in participants with BCG-unresponsive NMIBC. Additional objectives of the study include characterization of safety and tolerability, pharmacokinetics, potential predictive biomarkers, and changes in patient-reported outcomes (PRO) for quality of life assessments.

Intervention: Patients are administered nivolumab at
Primary Outcome Measures:
  Proportion of carcinoma in situ participants with complete response per pathology review committee.
  Duration of complete response, per pathology review committee, in carcinoma in situ participants with complete response
  Event free survival, per pathology review committee, for all non- carcinoma in situ participants.
Secondary Outcome Measures:
  Progression free survival, per pathology review committee, for all participants
  Overall safety and tolerability will be measured by the incidence of adverse events and serious adverse events, adverse events leading to discontinuation, immune-mediated adverse events, deaths, and laboratory abnormalities and changes from baseline.
Parallel Treatment Arms:
  Arm A: Nivolumab monotherapy. Patients will receive nivolumab at 480 mg intravenously once every four weeks for up to 52 weeks (12 months).
  Arm B: Nivolumab and BCG. Patients will receive nivolumab at 480 mg intravenously once every four weeks for up to 52 weeks (12 months). Patients will also receive intravesical BCG (induction) weekly for 6 weeks followed by maintenance intravesical BCG weekly for 3 weeks at 3 months, 6 months and 12 months following the first intravesical dose. The strain and dose used will be based on current standard of care (SOC) for the particular geographic region in which the participant is undergoing treatment.
  Arm C: Nivolumab and the compound of Formula I, or pharmaceutically acceptable salts thereof. Patients will receive nivolumab at 480 mg intravenously once every four weeks plus the compound of Formula (I), or pharmaceutically acceptable salts thereof, at 100 mg orally day for up to 52 weeks (12 months).
  Arm D: Nivolumab and compound of Formula I, or pharmaceutically acceptable salts thereof, and BCG. Patients will receive nivolumab at 480 mg intravenously once every four weeks plus the compound of Formula (I), or pharmaceutically acceptable salts thereof, at 100 mg orally day for up to 52 weeks (12 months). Patients will also receive intravesical BCG (induction) weekly for 6 weeks followed by maintenance intravesical BCG weekly for 3 weeks at 3 months, 6 months and 12 months following the first intravesical dose. The strain and dose used will be based on current standard of care (SOC) for the particular geographic region in which the participant is undergoing treatment.

Eligibility
Inclusion Criteria (Study Open to All Sexes, 18 Years and Older):
  Pathologically demonstrated BCG-unresponsive, high-risk NMIBC, where high-risk NMIBC is defined as carcinoma in situ (CIS) with or without papillary component, and any T1 or Ta high-grade lesions; where diagnosis is established within 8 weeks prior to starting treatment
  Predominant histologic component (>50%) must be urothelial (transitional cell) carcinoma.
  Participants must have undergone each of the following procedures within 8 weeks of randomization:
    Complete excision of all papillary disease (T1/TaHG). For participants with T1 lesions, a re-staging TURBT must be performed within 4 weeks after the initial TURBT to ensure that the pathology specimen contains muscularis propria that is free of invasive tumor per PRC.
    Resection or fulguration of all detectable CIS, if feasible. Florescence-guided cystoscopy is encouraged but not mandated.
    Random sampling of bladder mucosa for detection of occult CIS. The bladder must be mapped by visual inspection and random biopsies taken from the trigone, right and left lateral walls, posterior wall, dome and prostatic urethra. In addition, the presence of any suspicious lesions must be recorded and these lesions biopsied.
    Urine cytology obtained by bladder wash. Recognizing the possibility of occult CIS, cytology at screening does not need to be negative for study participation.
    Computed tomography (CT) scan of the chest and CT or magnetic resonance imaging (MRI) of the abdomen and pelvis and all other areas of suspected disease to exclude locally advanced or metastatic bladder cancer or synchronous UC in the upper urinary tracts within 90 days prior to randomization.
  Participants should either be deemed medically unfit for radical cystectomy, ro should have refused radical cystectomy after consultaion with their urologist or oncologist. Participants may be deemed medically unfit for radical cystectomy due to comorbid conditions with a risk of mortality from radical cystectomy >5% as estimated by the American College of Surgeons risk calculator using theprocedure terminology code 51595 or 51596 for cystectomy.
Exclusion Criteria:
  Women who are pregnant or breastfeeding.
  Participants with a personal or family (i.e., in a first-degree relative) history of cytochrome b6 reductase deficiency (previously called methomoglobine reductase deficiency) or other diseases that put them at risk for methomeoglobinemia. All participants will be screened for methemoglobin levels prior to randomization.
  Participants with a history of glucose-6-phosphate dehydrogenase (G6PD) deficiency or other congenital or autoimmune hemolytic disorders. All participants will be screened for G6PD levels prior to randomization.
  Evidence of locally advanced or metastatic bladder cancer as seen in cross-sectional imaging of the chest, abdomen, and pelvis.

UC in the upper genitourinary tract (kidneys, renal collecting systems, ureters) within 24 months of enrollment UC and/or CIS in the prostatic urethra within 12 months of enrollment Locally advanced disease demonstrated by pelvic examination preferably performed under anesthesia Previous or concurrent muscle invasive or disseminated/metastatic bladder cancer Prior treatment with an anti-PD-1, anti-programmed death ligand 1 (PD-L1), anti-PD-L2, or anti-cytotoxic T-lymphocyte-associated protein 4 (anti-CTLA-4) antibody, or any other antibody or drug specifically targeting T-cell co-stimulation or checkpoint pathways Prior treatment with the compound of Formula I or any other IDO1 inhibitors Prior systemic chemotherapy or immunotherapy. Intravesical chemotherapy and/or interferon administered prior to the date of tumor sample submission is permitted.

Prior radiation therapy for bladder cancer

Prior surgery for bladder cancer other than TURBT and/or bladder biopsies

Study Design

After a safety-lead in the BCG-containing arms, participants will be randomized to one of 4 parallel treatment arms. Sufficient, recent tumor tissue obtained within 8 weeks (56 days) prior to randomization from the recurrent tumor obtained at transurethral bladder tumor resection (TURBT) must be submitted (1) for review by the pathology review committee to confirm the diagnosis of recurrent high-risk NMIBC and exclude tumor invasion of the muscularis propria and (2) to the analytical testing laboratory for PD-L1 expression. If sufficient tissue is not available, either additional tissue will be requested from the site or a repeat TURBT will be required.

A 6-week safety lead-in will be conducted in participants randomized to receive BCG and nivolumab with or without the compound of Formula (I), or pharmaceutically acceptable salts thereof, (Arms B and D) to determine safe dose levels to be administered during the treatment phase.

Following the safety lead-in, participants with carcinoma in situ, with or without papillary disease, will be randomized in a 1:1:2:2 ratio into study Arms A through D. The study design is adaptive in nature in that an initial decision as to whether or not to continue a treatment arm to full enrollment will be made based on the results of complete response rate at 6 months in the first 27 CIS participants in each arm.

Arms that are chosen for expansion after meeting the target complete response rate at 6 months will proceed to full enrollment to include additional carcinoma in situ participants as well as non-carcinoma in situ participants (high grade Ta or any T1 NMIBC).

On-study cystoscopy and urinary cytology in all participants will begin 13 weeks following the first dose of nivolumab and will continue every 13 weeks thereafter. Bladder biopsies will be obtained at 26 weeks and 52 weeks after the first dose of nivolumab in carcinoma in situ participants.

Efficacy assessments should occur until disease recurrence or progression per pathology review committee, or until treatment discontinuation, whichever occurs later. Treatment beyond disease recurrence is not permitted except in the case of a low-grade Ta UC recurrence only.

Example 9: Compound of Formula I Administered in Combination with Relatlimab and Nivolumab in Patients with Advanced Malignant Tumors A non-limiting example of a Phase I/II clinical trial for patients with advanced malignant tumors involving the combination of the compound of Formula I, or pharmaceutically acceptable salts thereof, and nivolumab and relatlimab is described below.

Intervention: Patients are administered relatlimab at a specified dose at specified intervals in combination with nivolumab at a specified dose at specified intervals in further combination with the compound of Formula I at a specified dose as specified days. In some embodiments, the patients are administered relatlimab at a specified dose at specified intervals in combination with nivolumab at a specified dose at specified intervals in further combination with ipilimumab at a specified dose at specified intervals.

Primary Outcome Measures:

Number of clinical laboratory test abnormalities with a time frame of approximately 4 years.

Number of Adverse Events (AEs) with a time frame of approximately 4 years.

Number of Serious Adverse Events (SAEs) with a time frame of approximately 4 years.

Number of AEs meeting protocol defined dose-limiting toxicity (DLT) criteria with a time frame of up to 6 weeks.

Number of AEs leading to discontinuation and deaths with a time frame of approximately 4 years.

Objective Response Rate (ORR) with a time frame of approximately 4 years.

Disease Control Rate (DCR) with a time frame of approximately 4 years.

Median Duration of Response (mDOR) with a time frame of approximately 4 years.

Secondary Outcome Measures:

Progression free survival (PFS) with a time frame of up to 4 years.

Study Arms:

Experimental Arm A: relatlimab plus nivolumab plus a compound of Formula I, or salt thereof, at specified doses at specified intervals.

Experimental Arm B: relatlimab plus nivolumab plus ipilimumab at specified doses at specified intervals.

Eligibility:

Inclusion Criteria (Study Open to All Sexes, 18 Years and Older):

Histologic or cytological confirmation of an incurable solid malignancy that is advanced (metastatic and/or unresectable), with measurable disease per RECIST v1.1.

Available tumor tissue for biomarker analysis.

Eastern Cooperative Oncology Group Performance Status (ECOG) status of 0 or 1.

Exclusion Criteria:

Participants with known or suspected uncontrolled CNS metastases.

Participants with a history of interstitial lung disease (ILD)/pneumonitis.

Prior malignancy active within the previous 3 years except for locally curable cancers that have been cured, such as basal or squamous cell skin cancer.

Requirement for daily supplemental oxygen.

Example 10. Compound of Formula I Administered in Combination with Nivolumab in Patients with Advanced Bladder Cancer A non-limiting example of a clinical trial in patients with advanced bladder cancer involving the combination of a compound of Formula I, or pharmaceutically acceptable salts thereof, and nivolumab is described below.

Purpose: The purpose of the study is to, among other things, determine safety and effectiveness of a compound of Formula I (or salt thereof) when combined with nivolumab in patients with advanced bladder cancer.

Intervention: Patients were administered a compound of Formula I at a specified dose at specified intervals. The patients were also administered a nivolumab, which was administered at specified intervals.

Primary Outcome Measures:

Safety and tolerability of a compound of Formula I as measured by a composite of the incidence of adverse events (AEs), serious adverse events (SAEs), AEs leading to discontinuation, deaths, and clinical laboratory test abnormalities. The time frame is 100 days after the last dose of study therapy.

Safety of a compound of Formula I plus nivolumab as measured by a composite of the incidence of adverse events (AEs), serious adverse events (SAEs), AEs leading to discontinuation, deaths, and clinical laboratory test abnormalities. The time frame is 100 days after the last dose of study therapy.

Anti-tumor activity of a compound of Formula I administered in combination with nivolumab as measured by the best overall response (BOR) as measured by CT scan. The time frame is approximately 3 years.

Anti-tumor activity of a compound of Formula I administered in combination with nivolumab as measured by the duration of response (DOR) as measured by CT scan. The time frame is approximately 3 years.

Anti-tumor activity of a compound of Formula I administered in combination with nivolumab as measured by progression-free survival rates (PFSRs) as measured by CT scan. The time frame is approximately 3 years.

Secondary Outcome Measures

Maximum observed plasma concentration (C max) of a compound of Formula I as measured by plasma concentration with a time frame of approximately 3 years.

Time of maximum observed plasma concentration (T max) of a compound of Formula I as measured by plasma concentration with a time frame of approximately 3 years.

Area under the concentration-time curve from time zero extrapolated to infinite time [AUC(INF)] of a compound of Formula I as measured by plasma concentration with a time frame of approximately 3 years.

Area under the concentration-time curve from time zero to the time of the last quantifiable concentration [AUC(0-T)] of a compound of Formula I as measured by plasma concentration with a time frame of approximately 3 years.

Area under the concentration-time curve in 1 dosing interval [AUC(TAU)] of a compound of Formula I as measured by plasma concentration with a time frame of approximately 3 years.

Trough observed plasma concentration at the end of the dosing interval (Ctrough) of a compound of Formula I as measured by plasma concentration with a time frame of approximately 3 years.

Observed plasma concentration at 24 hours (C24) of a compound of Formula I as measured by plasma concentration with a time frame of approximately 3 years.

Apparent terminal phase half-life (T-HALF) of a compound of Formula I as measured by plasma concentration with a time frame of approximately 3 years.

Apparent total body clearance (CLT/F) of a compound of Formula I as measured by plasma concentration with a time frame of approximately 3 years.

Apparent renal clearance (CLR/F) of a compound of Formula I as measured by plasma concentration with a time frame of approximately 3 years.

Volume of distribution of terminal phase (Vz/F) of a compound of Formula I as measured by plasma concentration with a time frame of approximately 3 years.

Apparent volume of distribution at steady state (Vss/F) of a compound of Formula I as measured by plasma concentration with a time frame of approximately 3 years.

Accumulation index (AI) of a compound of Formula I as measured by plasma concentration with a time frame of approximately 3 years.

Percent urinary recovery (% UR) of a compound of Formula I as measured by urine concentration with a time frame of approximately 3 years.

Percent urinary recovery over 24 hours (% UR24) of a compound of Formula I as measured by urine concentration with a time frame of approximately 3 years.

Ratio of metabolite C max to parent C max, corrected for molecular weight (MR_C max) of a compound of Formula I as measured by plasma concentration with a time frame of approximately 3 years.

Ratio of metabolite AUC(0-T) to parent AUC(0-T), corrected for molecular weight (single dose in clinical pharmacology substudy only) [MR_AUC(0-T)] of a compound of Formula I as measured by plasma concentration with a time frame of approximately 3 years.

Ratio of metabolite AUC(TAU) to parent AUC(TAU), corrected for molecular weight [MR_AUC(TAU)] of a compound of Formula I as measured by plasma concentration with a time frame of approximately 3 years.

Ratio of metabolite AUC(INF) to parent AUC(INF), corrected for molecular weight (single dose in clinical pharmacology substudy only) [MR_AUC(INF)] of a compound of Formula I as measured by plasma concentration with a time frame of approximately 3 years.

Anti-drug antibody (ADA) response to nivolumab in combination with a compound of Formula I as measured by immunoassay and liquid chromatography-mass spectrometry with a time frame of approximately 3 years.

Experimental Treatment Arms

1. Combination Therapy (Dose Escalation). Participants with advanced cancers received a compound of Formula I orally (PO), daily (QD) at a dose of 25 mg, 50 mg, 100 mg or 200 mg for all advanced cancers over a 2 week lead-in period. Participants were then also administered nivolumab intravenously at a dose of 240 mg once every two weeks.

2. Combination Therapy (Dose Expansion). A total of 516 patients with advanced tumors were treated with the compound of Formula I and nivolumab at a dose of 100 or 200 mg orally once daily plus nivolumab at a dose of 240 mg intravenously once every two weeks (Q2W), including 30 participants with advanced bladder cancer. Three patients received the compound of Formula I alone. IDO1 inhibitor therapy is not permitted. Prior exposure to immune checkpoint inhibitors or therapy targeting T-cell costimulation requires a washout period of >4 weeks.

Eligibility

Inclusion Criteria (Study Open to All Sexes, 18 Years to 100 Years):

During dose escalation, subjects with advanced solid tumors that have progressed following at least one standard regimen.

During cohort expansion, subjects with advanced bladder cancer that either have received at least one prior therapy or are treatment naive.

Subjects must have measurable disease.

Subject must consent to provide previously collected tumor tissue and a tumor biopsy during screening.

At least 4 weeks since any previous treatment for cancer.

Must be able to swallow pills or capsules.

Eastern Cooperative Oncology Group (ECOG) Performance Status 0-1.

Exclusion Criteria:

Active or chronic autoimmune diseases.

Uncontrolled or significant cardiovascular disease.

History of any chronic Hepatitis, active Hepatitis B or C, human immunodeficiency virus (HIV), or acquired immune deficiency syndrome (AIDS).

Chronic hepatitis: Positive test for Hepatitis B virus surface antigen or Hepatitis C antibody (except for subjects with hepatocellular carcinoma).

Active central nervous system (CNS) metastases and CNS metastases as the only sites of disease.

Active infection.

Results

The majority of 30 patients with advanced bladder cancer had received 1 prior therapy (57%), which was most often cisplatin-based (77%); 3 patients received prior immuno-oncology (IO) therapy. The majority of patients (60%) had an ECOG performance status of 1. Patients had liver (33%) and other visceral (83%) metastases and most patients (73%) had 1 or 2 Bellmunt prognostic score risk factors. Approximately 50% of patients had PD-L1-positive tumors. Disease characteristics and prior therapy were similar among patients with advanced bladder cancer who received the 100-mg and 200-mg doses of the compound of Formula I.

As presented in Table 4, the median duration of treatment with the compound of Formula I was 8 weeks for patients with advanced bladder cancer and median duration of nivolumab treatment was 8.4 and 8.5 weeks, respectively. Also as presented in Table 4, most patients discontinued treatment due to disease progression. The median duration of follow up was 22 weeks for patients with advanced bladder cancer and 24 weeks for patients with IO-naive advanced bladder cancer (n=27).

TABLE 4

End of Treatment Disposition in all Patients with Advanced Bladder Cancer

| | Bladder cancer expansion cohort | | | | |
| --- | --- | --- | --- | --- | --- |
| | All patients (n = 30) | IO-naïve patients (n = 27) | Compound of Formula I (100 mg) + nivolumab[a] (n = 14) | Compound of Formula I (200 mg) + nivolumab[a] (n = 16) | All treated patients (n = 519)[b] |
| Median duration of therapy, weeks (min-max) | | | | | |
| Compound of Formula I | 8.0 (2.6-65.0) | 8.0 (3.0-65.0) | 9.95 (4.1-65.0) | 8.0 (2.6-54.1) | 8.0 (0.1-66.6)[c] |
| Nivolumab | 8.5 (4.0-66.6) | 10.0 (4.0-66.6) | 9.45 (6.0-66.6) | 8.1 (4.0-55.0) | 8.35 (2.0-68.0)[d] |
| Median duration of follow up, weeks (min-max) | 22.0 (4.0-64.0) | 24.0 (8.0-64.0) | 22.0 (8.0-64.0) | 23.0 (4.0-57.0) | 16.0 (0.0-83.0) |
| Continuing treatment, n (%)[e] | 8 (27) | 8 (29) | 4 (29) | 4 (25) | 151 (29) |
| Reasons for not completing planned treatment, n (%)[f] | | | | | |
| Disease progression | 17 (57) | 14 (52) | 9 (64) | 8 (50) | 262 (50) |
| AE unrelated to drug | 0 | 0 | 0 | 0 | 31 (6) |
| Study drug toxicity | 3 (10) | 3 (11) | 1 (7) | 2 (13) | 19 (4) |
| Withdrew consent | 0 | 0 | 0 | 0 | 6 (1) |
| Patient request | 1 (3) | 1 (4) | 0 | 1 (6) | 5 (<1) |
| No longer meets criteria | 0 | 0 | 0 | 0 | 3 (<1) |
| Death | 0 | 0 | 0 | 0 | 1 (<1)[g] |
| Lost to follow-up | 0 | 0 | 0 | 0 | 1 (<1) |
| Poor/noncompliance | 0 | 0 | 0 | 0 | 1 (<1) |
| Other | 0 | 0 | 0 | 0 | 2 (<1) |

[a]Nivolumab 240 mg Q2W;
[b]Three patients receive compound of Formula I only;
[c]Data based on 513 patients;
[d]Data based on 516 patients;
[e]Patients receive 24 weeks of planned initial treatment, and may then continue to receive additional treatment up to 96 weeks;
[f]Includes patients in either initial or additional treatment who did not complete planned treatment; an additional 9 patients (including 1 with IO-naïve bladder cancer treated with 200 mg compound of Formula I) completed planned treatment;
[g]Death was unrelated to study drug.

As presented in Table 5, the compound of Formula I was well tolerated in patients with advanced bladder cancer. The compound of Formula I was associated with lower frequency and severity of TRAEs and TRAEs leading to discontinuation than the 200-mg dose. No treatment-related deaths occurred in patients with advanced bladder cancer.

TABLE 5

TRAEs with the Compound of Formula I plus Nivolumab in Advanced Bladder Cancer and in all treated patients

| | All treated patients | | | | | | | | |
|---|---|---|---|---|---|---|---|---|---|
| | All patients (n = 516)[a] | | | Compound of Formula I (100 mg) + nivolumab (n = 420) | | | Compound of Formula I (200 mg) + nivolumab (n = 70) | | |
| | Any grade | Grade 3-4 | Grade 5 | Any grade | Grade 3-4 | Grade 5 | Any grade | Grade 3-4 | Grade 5 |
| Any TRAE, n (%) | 294 (57) | 61 (12) | 3 (<1)[b] | 230 (55) | 41 (10) | 3 (1)[b] | 51 (73) | 19 (27) | 0 |
| TRAEs in ≥10% of bladder cancer patients, n (%) | | | | | | | | | |
| Fatigue | 79 (15) | 3 (<1) | 0 | 60 (14) | 1 (<1) | 0 | 15 (21) | 2 (3) | 0 |
| Nausea | 63 (12) | 2 (<1) | 0 | 47 (11) | 1 (<1) | 0 | 12 (17) | 1 (1) | 0 |
| Serious TRAEs, n (%) | 37 (7) | 24 (5) | 3 (<1)[b] | 29 (7) | 18 (4) | 3 (<1)[b] | 7 (10) | 6 (9) | 0 |
| TRAEs leading to treatment discontinuation, n (%) | 19 (4) | 11 (2) | 3 (<1)[b] | 12 (3) | 6 (1) | 3 (<1)[b] | 7 (10) | 5 (7) | 0 |
| | Bladder cancer expansion cohort | | | | | | | | |
| | All patients (n = 30) | | | Compound of Formula I (100 mg) + nivolumab (n = 14) | | | Compound of Formula I (200 mg) + nivolumab (n = 16)[c] | | |
| | Any grade | Grade 3-4 | Grade 5 | Any grade | Grade 3-4 | Grade 5 | Any grade | Grade 3-4 | Grade 5 |
| Any TRAE, n (%) | 21 (70) | 11 (37)[d,e] | 0 | 8 (57) | 3 (21)[d] | 0 | 13 (81) | 8 (50)[e] | 0 |
| TRAEs in ≥10% of bladder cancer patients, n (%) | | | | | | | | | |
| Fatigue | 8 (27) | 2 (7) | 0 | 1 (7) | 0 | 0 | 7 (44) | 2 (13) | 0 |
| Decreased appetite | 5 (17) | 1 (3) | 0 | 0 | 0 | 0 | 5 (31) | 1 (6) | 0 |
| Autoimmune hep. | 4 (13) | 4 (13) | 0 | 1 (7) | 1 (7) | 0 | 3 (19) | 3 (19) | 0 |
| Nausea | 4 (13) | 1 (3) | 0 | 0 | 0 | 0 | 4 (25) | 1 (6) | 0 |
| ALT increased | 3 (10) | 1 (3) | 0 | 1 (7) | 1 (7) | 0 | 2 (13) | 0 | 0 |
| AST increased | 3 (10) | 1 (3) | 0 | 1 (7) | 1 (7) | 0 | 2 (13) | 0 | 0 |
| Pyrexia | 3 (10) | 0 | 0 | 1 (7) | 0 | 0 | 2 (13) | 0 | 0 |
| Serious TRAEs, n (%) | 4 (13) | 3 (10) | 0 | 2 (14) | 1 (7) | 0 | 2 (13) | 2 (13) | 0 |
| TRAEs leading to treatment discontinuation, n (%) | 4 (13) | 3 (10) | 0 | 1 (7) | 1 (7) | 0 | 3 (19) | 2 (13) | 0 |

[a]Includes all patients who received ≥1 does of compound of Formula I and nivolumab;

[b]Includes Stevens-Johnson syndrome (n = 1), histiocytosis haemophagic (n = 1; initially reported as grade 5 but then downgraded to grade 4 because patient died due to concurrent unrelated grade 5 even (sepsis) and myocarditis (n = 1);

[c]Nivolumab 240 mg Q2W;

[d]Other grade 3-4 TRAEs not shown in table include hypophosphatemia (n = 1);

[e]Other grade 3-4 TRAEs not shown in table include lipase increased (n = 1), hepatotoxicity (n = 1), anemia (n = 1), and maculopapular rash (n = 1). ALT = alanine aminotransferase, AST = aspartate aminotransferase.

As depicted in Table 6, ORR and DCR in patients with IO-naive advanced bladder cancer (n=27) were 37% and 56%, respectively. ORRs were similar in the 100- and 200-mg dose cohorts. Additionally, ORR and DCR were higher in patients with PD-L1-positive vs PD-L1-negative tumors. Of the 3 patients who had received prior I-O therapy, 2 patients had progressive disease, and 1 patient died prior to disease assessment.

was observed that administration of 100 mg of the compound of Formula I was associated with improved tolerability vs the 200-mg dose. Additionally, the combination of the compound of Formula I and nivolumab demonstrated preliminary antitumor activity in patients with advanced bladder cancer, including those with liver and other visceral metastases. ORR of 37% and DCR of 56% were observed in all IO-naïve patients. For PD-L1-positive IO-naïve patients,

TABLE 6

Response with Compound of Formula I plus Nivolumab in IO-Naïve Advanced Bladder Cancer

| BOR, n (%) | All IO-naive patients (n = 27) | 100 mg plus nivolumab (n = 13)[a] | 200 mg plus nivolumab (n = 14)[a] | PD-L1 positive (n = 14) | PD-L1 negative (n = 10) |
|---|---|---|---|---|---|
| CR | 3 (11) | 0 | 3 (21) | 2 (14) | 1 (10) |
| PR | 7 (26) | 5 (38) | 2 (14) | 5 (36) | 2 (20) |
| SD | 5 (19) | 1 (8) | 4 (29) | 2 (14) | 2 (20) |
| PD | 12 (44) | 7 (54) | 5 (36) | 5 (36) | 5 (50) |
| Death prior to disease assessment/unable to determine | 0 | 0 | 0 | 0 | 0 |
| ORR, % (95% CI) | 37 (19.4, 57.6) | 38 (13.9, 68.4) | 36 (12.8, 64.9) | 50 (23.0, 77.0) | 30 (6.7, 65.2) |
| DCR, %[b] (95% CI) | 56 (35.3, 74.5) | 46 (19.2, 74.9) | 64 (35.1, 87.2) | 64 (35.1, 87.2) | 50 (18.7, 81.3) |

[a]nivolumab 240 mg Q2W;
[b]DCR = CR + PR + SD; BOR = best overall response; CR = complete response; DCR = disease control rate; PD = progressive disease; PR = partial response; SD = stable disease.

Table 7 shows response and disease control in select patient subgrounds in patients with IO-naïve advanced bladder cancer. The clinical benefit was higher in patients with fewer Bellmunt prognostic score risk factors; however, approximately 33% of patients with liver and 30% of patients with visceral metastases responded.

an ORR of 50% and a DCR of 64% was observed. For IO-naïve patients with baseline liver metastasis, an ORR of 33% and a DCR of 44% was observed. These responses were generally observed by the first imaging evaluation (8 weeks) and were durable. Finally, efficacy appears similar for the 100-mg and 200-mg doses of the compound of

TABLE 7

Response with Compound of Formula I plus Nivolumab in IO-Naïve Advanced Bladder Cancer in Select Patient Subgroups

| | Prior line(s) of therapy | | Baseline lymph node only | | Baseline visceral metastases | | Baseline liver metastases | | Bellmunt risk factors | | |
|---|---|---|---|---|---|---|---|---|---|---|---|
| | ≤1 n = 17 | ≥2 n = 10 | Yes n = 3 | No n = 24 | Yes n = 23 | No n = 4 | Yes n = 9 | No n = 18 | 0 n = 6 | 1 n = 11 | 2 n = 8 |
| ORR, % (95% CI) | 35 (14.2, 61.7) | 40 (12.2, 73.8) | 67 (9.4, 99.2) | 33 (15.6, 55.3) | 30 (13.2, 52.9) | 75 (7.5, 70.1) | 33 (17.3, 64.3) | 39 (14.2, 61.7) | 50 (11.8, 88.2) | 36 (10.9, 69.2) | 38 (8.5, 75.5) |
| DCR, % (95% CI) | 47 (23.0, 72.2) | 70 (34.8, 93.3) | 67 (9.4, 99.2) | 54 (32.8, 74.4) | 52 (30.6, 73.2) | 75 (19.4, 99.4) | 44 (13.7, 78.8) | 61 (35.7, 82.7) | 67 (22.3, 95.7) | 64 (30.8, 89.1) | 38 (8.5, 75.5) |

For all IO-naïve patients, median time to response was 7.8 weeks (range: 7.0-23.3 weeks) and median duration of response was not reached (range: 16.1-51.7+ weeks), with results similar at the 100- and 200-mg doses of the compound of Formula I. Change in tumor burden over time and time to and duration of response with compound of Formula I and nivolumab are shown in FIG. 4A-B and FIG. 5A-B. Responses were deep and durable, with some lasting beyond treatment discontinuation. More patients with PD-L1-positive vs PD-L1-negative tumors had durable responses.

The clinical trial results demonstrate that the combination of the compound of Formula I and nivolumab demonstrated a favorable safety profile in heavily pretreated patients. It Formula I. The data support further development of the compound of formula I plus nivolumab in urothelial carcinoma.

Embodiments

The following list of embodiments is intended to complement, rather than displace or supersede, the previous descriptions.

EMBODIMENT 1. A method of treating cancer in a subject comprising administering to the subject a combination of a monoclonal antibody and a compound of Formula I, or a pharmaceutically acceptable salt thereof, or a combination thereof,

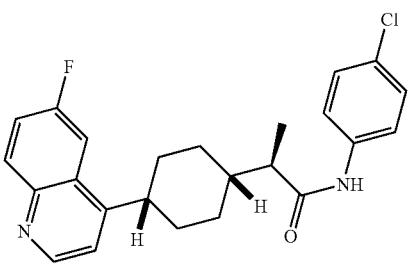

(I)

wherein the amount of the compound administered to the subject is from about 100 mg per day to about 200 mg per day and optionally wherein the subject exhibits improved anti-tumor activity as measured by objective response rate, duration of response, and progression-free survival rate.

EMBODIMENT 2. The method of embodiment 1, wherein the cancer is a malignant solid tumor or a liquid tumor, for example, lymphoma.

EMBODIMENT 3. The method of embodiment 1 or 2, wherein the cancer is metastatic and/or unresectable.

EMBODIMENT 4. The method of any one of the preceding embodiments, wherein the cancer is recurrent.

EMBODIMENT 5. The method of any one of the preceding embodiments, wherein the cancer is melanoma, non-small cell lung cancer, squamous cell carcinoma of the head and neck, bladder cancer, renal cell carcinoma, cervical cancer, pancreatic cancer, ASST, diffuse large B-cell lymphoma, or gastric cancer.

EMBODIMENT 6. The method of any one of the preceding embodiments, wherein the cancer has active brain metastases.

EMBODIMENT 7. The method of any one of the preceding embodiments, wherein the subject has received at least one prior therapy for the treatment of the cancer, for example, intravesical bacillus Calumette-Guerin (BCG) therapy.

EMBODIMENT 8. The method of any one of embodiments 1 to 6, wherein the subject is treatment naïve.

EMBODIMENT 9. The method of any one of the preceding embodiments, wherein the subject exhibits an Eastern Cooperative Oncology Group (ECOG) performance status of less than or equal to 1, less than or equal to 2, or less than or equal to 3 following administration.

EMBODIMENT 10. The method of any one of the preceding embodiments, wherein the compound is

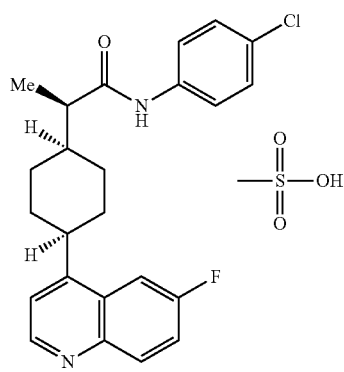

or wherein the compound is the free base form of

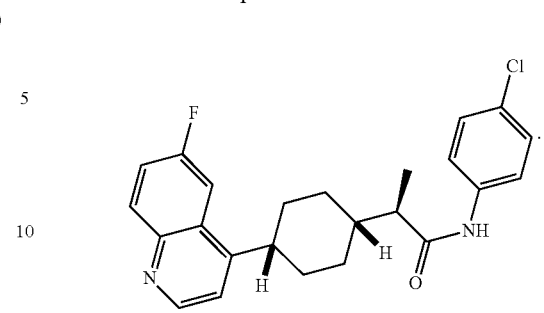

EMBODIMENT 11. The method of any one of the preceding embodiments, wherein the subject is a human, preferably an adult.

EMBODIMENT 12. The method of any one of the preceding embodiments, wherein the monoclonal antibody is an anti-PD-1 antibody, an anti-CTLA-4 antibody, an anti-Lag-3 antibody, or a combination thereof, for example, wherein the monoclonal antibody is nivolumab, nivolumab and ipilimumab, or nivolumab and relatlimab.

EMBODIMENT 13. The method of embodiment 12, wherein the nivolumab is administered by intravenous infusion at a dose of about 80 mg every 3 weeks; about 240 mg every 2 weeks; about 360 mg every 3 weeks; or about 480 mg every 4 weeks, or wherein the ipilimumab is administered by intravenous infusion at a dose of about 3 mg/kg every 3 weeks; about 1 mg/kg every 6 weeks; or about 1 mg/kg every 8 weeks.

EMBODIMENT 14. The method of any one of the preceding embodiments, wherein the treatment does not result in a grade 4 or grade 5 adverse event or wherein the treatment results in no more than a grade 1 adverse event or wherein the treatment results in no more than a grade 2 adverse event or wherein the treatment results in no more than a grade 3 adverse event.

EMBODIMENT 15. The method of any one of the preceding embodiments, further comprising administration of an additional chemotherapeutic agent, for example a platinum-based chemotherapeutic agent, such as platinum-based doublet chemotherapy.

What is claimed is:

1. A method of treating cancer in a subject comprising administering to the subject a combination of nivolumab and a compound of Formula I, or a pharmaceutically acceptable salt thereof, or a combination thereof,

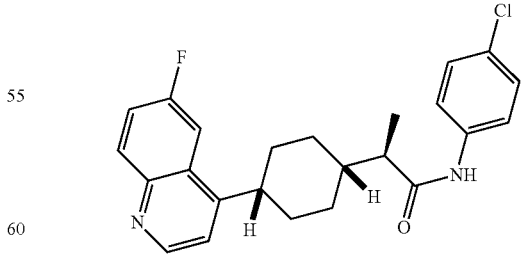

(I)

wherein the amount of the compound administered to the subject is from about 100 mg per day to about 200 mg per day and optionally wherein the subject exhibits improved anti-tumor activity as measured by objective response rate, duration of response, and progression-free survival rate;

wherein the nivolumab is administered by intravenous infusion at a dose of about 80 mg every 3 weeks; about 240 mg every 2 weeks; about 360 mg every 3 weeks; or about 480 mg every 4 weeks;

wherein the cancer is lymphoma, melanoma, non-small cell lung cancer, squamous cell carcinoma of the head and neck, bladder cancer, renal cell carcinoma, cervical cancer, pancreatic cancer, ASST, diffuse large B-cell lymphoma, gastric cancer or a cancer that has active brain metastases.

2. The method of claim 1, wherein the cancer is a malignant solid tumor or a liquid tumor.

3. The method of claim 1, wherein the cancer is metastatic and/or unresectable.

4. The method of claim 1, wherein the cancer is recurrent.

5. The method of claim 1, wherein the subject has received at least one prior therapy for the treatment of the cancer.

6. The method of claim 1, wherein the subject is treatment naïve.

7. The method of claim 1, wherein the subject exhibits an Eastern Cooperative Oncology Group (ECOG) performance status of less than or equal to 1, less than or equal to 2, or less than or equal to 3 following administration.

8. The method of claim 1, wherein the compound is

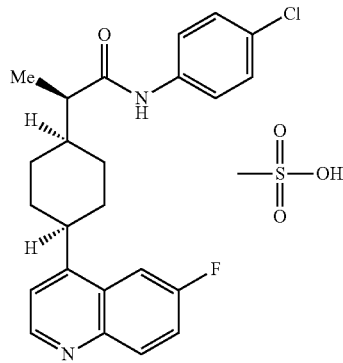

or wherein the compound is the free base form of

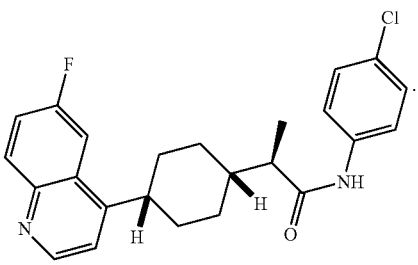 [SMILES: C[C@@H](C(=O)Nc1ccc(Cl)cc1)[C@H]1CC[C@@H](c2ccnc3ccc(F)cc32)CC1]

9. The method of claim 1, wherein the subject is a human.

10. The method of claim 1, wherein the treatment does not result in a grade 4 or grade 5 adverse event or wherein the treatment results in no more than a grade 1 adverse event or wherein the treatment results in no more than a grade 2 adverse event or wherein the treatment results in no more than a grade 3 adverse event.

11. The method of claim 1, further comprising administration of an additional chemotherapeutic agent.

12. The method of claim 1, wherein the nivolumab is administered by intravenous infusion at a dose of about 80 mg every 3 weeks.

13. The method of claim 1, wherein the nivolumab is administered by intravenous infusion at a dose of about 240 mg every 2 weeks.

14. The method of claim 1, wherein the nivolumab is administered by intravenous infusion at a dose of; about 360 mg every 3 weeks.

15. The method of claim 1, wherein the nivolumab is administered by intravenous infusion at a dose of about 480 mg every 4 weeks.

16. The method of claim 5, wherein the at least one prior therapy for the treatment of the cancer is intravesical bacillus Calumette-Guerin (BCG) therapy.

17. The method of claim 9, wherein the human is an adult.

18. The method of claim 11, wherein the additional chemotherapeutic agent is a platinum-based chemotherapeutic agent.

19. The method of claim 18, wherein the platinum-based chemotherapeutic agent is a platinum-based doublet chemotherapy.

* * * * *

UNITED STATES PATENT AND TRADEMARK OFFICE
CERTIFICATE OF CORRECTION

PATENT NO. : 11,351,163 B2
APPLICATION NO. : 16/649277
DATED : June 7, 2022
INVENTOR(S) : Paul Basciano et al.

It is certified that error appears in the above-identified patent and that said Letters Patent is hereby corrected as shown below:

On the Title Page

Column 2 (Item (56) Other publications), Line 3, delete "Biologies"," and insert -- Biologics", --.

In the Claims

In Claim 16, Column 48, Line 38, delete "Calumette-" and insert -- Calmette- --.

Signed and Sealed this
Fourteenth Day of March, 2023

*Katherine Kelly Vidal*

Katherine Kelly Vidal
*Director of the United States Patent and Trademark Office*